(12) United States Patent
Skiba et al.

(10) Patent No.: US 7,662,176 B2
(45) Date of Patent: Feb. 16, 2010

(54) FOOTWEAR APPARATUS AND METHODS OF MANUFACTURE AND USE

(75) Inventors: Jeffry B. Skiba, Chandler, AZ (US); Lawrence A. Schneider, Scottsdale, AZ (US)

(73) Assignee: Vomaris Innovations, Inc., Chandler, AZ (US)

( * ) Notice: Subject to any disclaimer, the term of this patent is extended or adjusted under 35 U.S.C. 154(b) by 402 days.

(21) Appl. No.: 11/506,608

(22) Filed: Aug. 18, 2006

(65) Prior Publication Data
US 2007/0088341 A1   Apr. 19, 2007

Related U.S. Application Data

(63) Continuation-in-part of application No. 11/061,235, filed on Feb. 18, 2005, which is a continuation-in-part of application No. 10/784,088, filed on Feb. 19, 2004, now Pat. No. 7,457,667.

(51) Int. Cl.
*A61N 1/00* (2006.01)
(52) U.S. Cl. .................. 607/1; 607/2; 607/111; 607/144
(58) Field of Classification Search .............. 607/1–2, 607/111, 144
See application file for complete search history.

(56) References Cited

U.S. PATENT DOCUMENTS

| 116,562 A | 7/1871 | Collins |
|---|---|---|
| 167,162 A | 8/1875 | French |
| 175,974 A | 4/1876 | Hall |
| 222,276 A | 12/1879 | Hunter |
| 393,741 A | 12/1888 | Collins |
| 4,034,750 A | 7/1977 | Seiderman |
| 4,142,521 A | 3/1979 | Konikoff |
| 4,528,265 A | 7/1985 | Becker |
| 4,529,623 A | 7/1985 | Maggs |
| 4,569,673 A | 2/1986 | Tesi |
| 4,585,652 A | 4/1986 | Miller et al. |
| 4,657,808 A | 4/1987 | Maggs |
| 4,767,401 A | 8/1988 | Seiderman |

(Continued)

FOREIGN PATENT DOCUMENTS

GB     1588933     4/1981

(Continued)

OTHER PUBLICATIONS

"A powerful combination for the care of chronic wounds", http://www.jnjgateway.com/home.jhtml?loc=USENG&page=viewContent&contentId=090..., (observed Jan. 13, 2005), 2 pages.

(Continued)

*Primary Examiner*—Carl H Layno
*Assistant Examiner*—Deborah Malamud
(74) *Attorney, Agent, or Firm*—Maschkow & Gresham, P.L.C.

(57) ABSTRACT

A footwear apparatus includes multiple first reservoirs and multiple second reservoirs joined with a substrate. Selected ones of the multiple first reservoirs include a reducing agent, and first reservoir surfaces of selected ones of the multiple first reservoirs are proximate to a first substrate surface. Selected ones of the multiple second reservoirs include an oxidizing agent, and second reservoir surfaces of selected ones of the multiple second reservoirs are proximate to the first substrate surface.

3 Claims, 15 Drawing Sheets

U.S. PATENT DOCUMENTS

| | | | |
|---|---|---|---|
| 4,817,594 A | 4/1989 | Juhasz | |
| 4,937,323 A | 6/1990 | Silver et al. | |
| 5,053,001 A | 10/1991 | Reiler et al. | |
| 5,288,289 A | 2/1994 | Haak et al. | |
| 5,298,017 A | 3/1994 | Theeuwes et al. | |
| 5,322,520 A | 6/1994 | Milder | |
| 5,360,440 A | 11/1994 | Andersen | |
| 5,405,317 A | 4/1995 | Myers et al. | |
| 5,454,886 A | 10/1995 | Burrell et al. | |
| 5,681,575 A | 10/1997 | Burrell et al. | |
| 5,685,837 A | 11/1997 | Horstmann | |
| 5,695,857 A | 12/1997 | Burrell et al. | |
| 5,741,224 A | 4/1998 | Milder | |
| 5,753,251 A | 5/1998 | Burrell et al. | |
| 5,759,564 A | 6/1998 | Milder | |
| 5,770,255 A | 6/1998 | Burrell et al. | |
| 5,782,788 A | 7/1998 | Widemire | |
| 5,814,094 A | 9/1998 | Becker | |
| 5,837,275 A | 11/1998 | Burrell et al. | |
| 5,855,570 A * | 1/1999 | Scherson et al. | 604/304 |
| 5,944,685 A | 8/1999 | Muroki | |
| 5,958,440 A | 9/1999 | Burrell et al. | |
| 5,985,308 A | 11/1999 | Burrell et al. | |
| 6,017,553 A | 1/2000 | Burrell et al. | |
| 6,080,490 A | 6/2000 | Burrell et al. | |
| 6,087,549 A | 7/2000 | Flick | |
| 6,181,963 B1 | 1/2001 | Chin et al. | |
| 6,238,686 B1 | 5/2001 | Burrell et al. | |
| 6,306,419 B1 | 10/2001 | Vachon | |
| 6,333,093 B1 | 12/2001 | Burrell et al. | |
| 6,365,220 B1 | 4/2002 | Burrell et al. | |
| 6,522,918 B1 | 2/2003 | Crisp et al. | |
| 6,582,713 B2 | 6/2003 | Newell et al. | |
| 6,723,350 B2 | 4/2004 | Burrell et al. | |
| 6,738,662 B1 | 5/2004 | Frank | |
| 6,788,978 B2 | 9/2004 | Vesnaver | |
| 6,861,570 B1 | 3/2005 | Flick | |
| 2002/0122787 A1 | 9/2002 | Newell et al. | |
| 2002/0161405 A1 | 10/2002 | Drake | |
| 2002/0188282 A1 | 12/2002 | Greenberg | |
| 2003/0144723 A1 | 7/2003 | Andino et al. | |
| 2004/0015223 A1 | 1/2004 | Andino et al. | |
| 2004/0030276 A1 | 2/2004 | Flick | |
| 2004/0049145 A1 | 3/2004 | Flick | |
| 2004/0059282 A1 | 3/2004 | Flock et al. | |
| 2004/0167461 A1 | 8/2004 | Nitzan et al. | |
| 2004/0193089 A1 | 9/2004 | Fischer et al. | |
| 2004/0199086 A1 | 10/2004 | Crisp | |
| 2004/0267169 A1 | 12/2004 | Sun et al. | |
| 2004/0267231 A1 | 12/2004 | Sun et al. | |
| 2004/0267232 A1 | 12/2004 | Sun et al. | |
| 2004/0267237 A1 | 12/2004 | Sun et al. | |
| 2005/0004506 A1 | 1/2005 | Gyory | |
| 2005/0004508 A1 | 1/2005 | Sun et al. | |
| 2005/0004509 A1 | 1/2005 | Sun et al. | |
| 2005/0004550 A1 | 1/2005 | Sun et al. | |
| 2005/0010161 A1 | 1/2005 | Sun et al. | |
| 2005/0010192 A1 | 1/2005 | Sun et al. | |
| 2005/0015042 A1 | 1/2005 | Sun et al. | |
| 2005/0085751 A1 | 4/2005 | Daskal et al. | |
| 2005/0125006 A1 | 6/2005 | Nady | |
| 2005/0125009 A1 | 6/2005 | Perry et al. | |
| 2005/0125012 A1 | 6/2005 | Houser et al. | |
| 2005/0125016 A1 | 6/2005 | Trerotola | |
| 2005/0125018 A1 | 6/2005 | Galloway et al. | |
| 2005/0125021 A1 | 6/2005 | Nance et al. | |
| 2005/0148996 A1 | 7/2005 | Sun et al. | |
| 2005/0187580 A1 | 8/2005 | Skiba | |

FOREIGN PATENT DOCUMENTS

| | | |
|---|---|---|
| JP | 03-080874 A2 | 4/1991 |
| WO | WO-01/2157 A1 | 2/2001 |
| WO | WO-2004022033 A1 | 3/2004 |

OTHER PUBLICATIONS

"Managing chronic wounds", http://wound.smith-nephew.com/us/node.asp?NodeId=2871, (Observed Jan. 13, 2005), 2 pages.

"Silver-Powered Antimicrobial Dressing", http://www.convatec.com/ag/us/index.html?ref=brandsite, (Observed Jan. 13, 2005), 1 page.

* cited by examiner

FOOTWEAR APPARATUS AND METHODS OF MANUFACTURE AND USE

CROSS-REFERENCE TO RELATED APPLICATION

The present application is a continuation-in-part of U.S. patent application Ser. No. 11/061,235, filed Feb. 18, 2005, which is a continuation-in part of U.S. patent application Ser. No. 10/784,088, filed Feb. 19, 2004 now U.S. Pat. No. 7,457,667, which applications are hereby incorporated by reference.

BACKGROUND

Feet, toes, ankles, and lower legs commonly are injured and/or exposed to various bacteria, viruses, fungi, and other organisms or organic matter. In some cases, an injury or exposure to a microbe may result in compromised/damaged tissue, discomfort, infection, and/or colonization. In other cases, infected injuries or microbes may cause unpleasant odors or altered appearances.

DETAILED DESCRIPTION

Figure 1:
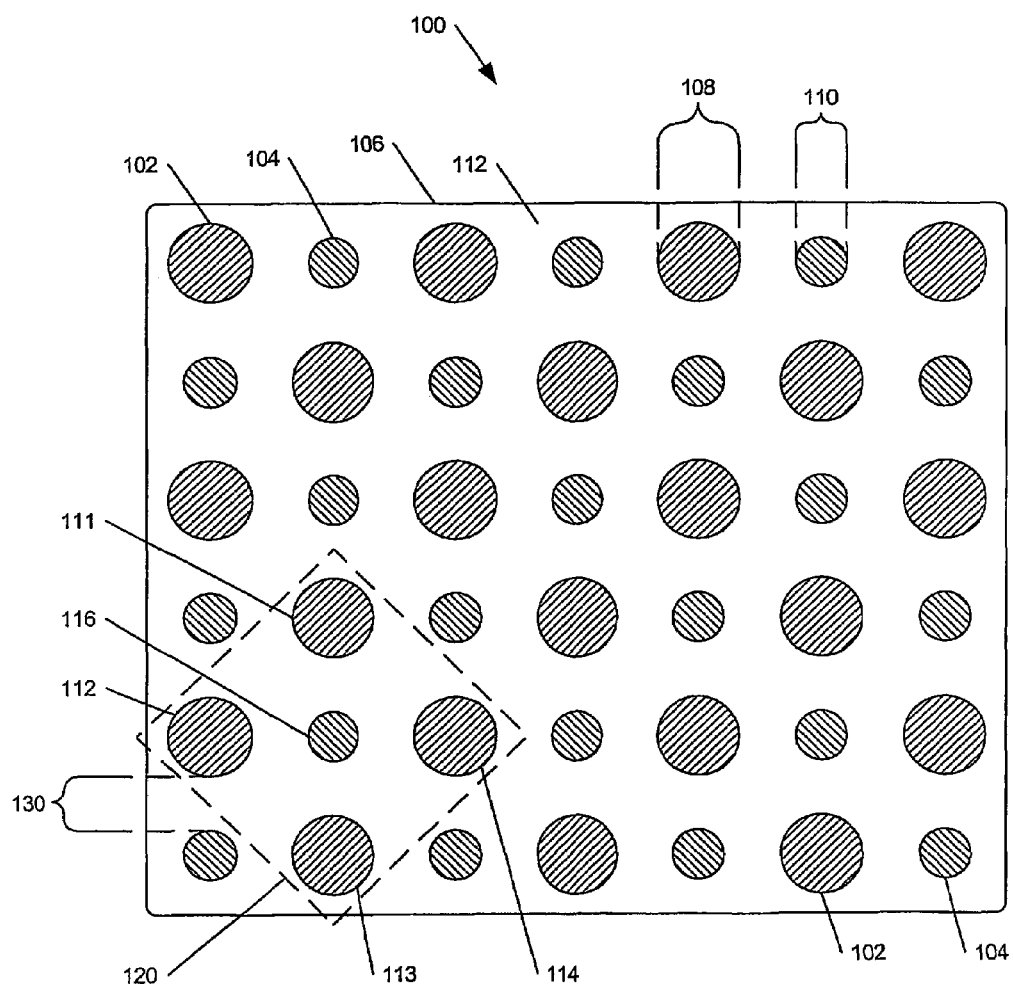
FIG. 1 is a top view of a portion of a footwear apparatus having a first configuration of dissimilar reservoirs, in accordance with an example embodiment.

Various embodiments, which may be referred to as "footwear apparatus," are described herein. In addition, various embodiments of methods for manufacturing portions of footwear apparatus and methods for using footwear apparatus are described herein. As used herein, the term "foot" includes, but is not limited to, a bodily area that includes one or more of a foot, a toe, a heel, an ankle, and a lower leg. The term "footwear apparatus" may be defined, in some embodiments, as apparatus that may directly or indirectly contact an area of "target tissue" on or in proximity to a foot. The term "footwear apparatus" may include, but is not limited to, one or more apparatus selected from a group of apparatus that includes a shoe, a shoe component, a shoe insert, a sock, and/or a therapeutic foot apparatus, for example. The term "shoe" includes, but is not limited to, an athletic shoe, a sneaker, a dress shoe, a salon shoe, a loafer, a boot, a sandal, a water shoe, water fins (e.g., snorkeling fins), a specialty shoe (e.g., a military shoe/boot, medical personnel footwear, a construction shoe/boot, an operating room shoe, a golf shoe, a bowling shoe, a biking shoe, a track shoe, etc.), a waterproof shoe, a medical shoe for treatment of a malady (e.g., maladies discussed later), and/or a slipper, for example. A "shoe component" includes, but is not limited to, an upper, a midsole, an outsole, an insole, a liner, and/or a tongue, for example. A "shoe insert" includes, but is not limited to, a shoe pad, an insole, an arch support, an arch cushion, a heel cushion, a heel cup, a heel pad, a heel protector, a forefoot pad, a plantar pad, a dorsal foot pad, an orthotic device, a liner, a metatarsal pad, an insert portion of a shoe tree, and/or a shoe storage insert, for example. A "sock" includes, but is not limited to, a sock, a stocking, an ankle brace and/or sleeve, a foot brace and/or sleeve, a bunion brace and/or sleeve, an arch brace and/or sleeve, a toe(s) cot, a toe(s) sleeve, a venous anti-embolic stocking, and/or a pressure gradient stocking, for example. A "therapeutic foot apparatus" includes, but is not limited to, a callus cushion, a callus remover, a corn cushion, a corn remover, a wart remover, a blister pad, moleskin, an antimicrobial treatment barrier, a thin film (e.g., a self-adhesive thin film), and/or a cushioning pad, for example.

Various embodiments include footwear apparatus that may, under certain circumstances, produce an electrical stimulus, and/or may electromotivate, electroconduct, elecrtroinduct, electrotransport, and/or electrophorese one or more therapeutic materials in areas of target tissue (e.g., iontophoresis), and/or may cause one or more biologic or other materials in proximity to, on or within target tissue to be affected (e.g., attract, repel, kill, neutralize, or alter cellular growth/viability/mobility, etc.). In various embodiments, a footwear apparatus may include "discrete reservoirs," which may be joined with one or more substrates. The term "discrete reservoir" may be defined, in some embodiments, as a mass of material, which has a boundary. A "mass of material" may include a bounded collection of one or more bulk materials, one or more material layers, and/or one or more threads or wires. The shape of a reservoir boundary may vary significantly, in various embodiments. Accordingly, although illustrated embodiments include reservoirs having various boundary configurations and cross-sectional shapes, it is to be understood that the inventive subject matter includes embodiments with reservoirs having other boundary configurations and cross-sectional shapes, as well. Further, although the term "substrate" may be used herein in a singular tense, it is to be understood that, in various embodiments, an apparatus may include a substrate having multiple interconnected or disjointed substrate surfaces. Accordingly, embodiments having multiple substrate surfaces are intended to be included within the scope of the inventive subject matter. Additionally, although various substrates are discussed herein, in some embodiments, a substrate may be an area of target tissue (e.g., reservoirs may be printed, tattooed, painted or otherwise directly applied to a portion of a foot or other bodily area).

Embodiments described herein include, but are not limited to, footwear apparatus having two types of dissimilar reservoirs, where a reservoir of a first type may establish a first portion of a battery cell, and a reservoir of a second type may establish a second portion of a battery cell. In various embodiments, one or more reservoirs of a first type are configured with (e.g., positioned in spaced relation with) one or more reservoirs of a second, dissimilar type. The term "spaced relation" may be defined, in some embodiments, as having an orientation with respect to each other in space, which orientation may be touching or not touching. The term "co-planar spaced relation" may be defined, in some embodiments, as having an orientation with respect to each other substantially across a same plane. It is to be understood that a "plane" may be a substantially flat surface, or a surface that is curved or bent. The term "spaced apart relation" may be defined, in some embodiments, as having a non-touching orientation with respect to each other in space. The term "co-planar spaced apart relation" may be defined, in some embodiments, as having a non-touching orientation with respect to each other substantially across a same plane. The terms "dissimilar type" and "dissimilar reservoirs" may be defined, in some embodiments, as reservoirs having material compositions that differ in the materials included in the reservoirs and/or the proportions of materials included in the reservoirs. The terms "similar type" and "similar reservoirs" may be defined, in some embodiments, as reservoirs having material compositions that are substantially the same in the materials included in the reservoirs and/or the proportions of materials included in the reservoirs.

It is to be understood that, in other embodiments, a footwear apparatus may include reservoirs of only one type, or a footwear apparatus may include reservoirs of more than two dissimilar types. For example, in an embodiment where one or more reservoirs of only one similar type are included in an apparatus, and dissimilar reservoirs are not included, selected ones of the one or more similar reservoirs each may form one portion of a cell, and an area of target tissue in proximity to the apparatus may itself form a second portion of the cell. In addition, it is to be understood that the illustrated embodiments are for example purposes, and accordingly footwear apparatus having different configurations of reservoirs from those illustrated herein are intended to be included within the scope of the inventive subject matter. Accordingly, it is to be understood that the illustrated embodiments are for the purpose of example, and should not be construed to limit the scope of the inventive subject matter to those illustrated embodiments.

It is to be understood that the use of oppositely-oriented cross-hatching in the Figures, in conjunction with first and second reservoirs, is not meant to imply that the first and second reservoirs are formed from or include conductive metals, although either or both may be formed from or include conductive metals. Instead, the use of oppositely-oriented cross-hatching in the Figures is used to indicate that the reservoirs are dissimilar.

FIG. 1 is a top view of a portion of a footwear apparatus 100 having a first configuration of dissimilar reservoirs, in accordance with an example embodiment. In particular, footwear apparatus 100 includes multiple first discrete reservoirs 102 and multiple second discrete reservoirs 104 joined with a substrate 106. Various materials that may be used to form first discrete reservoirs, second discrete reservoirs, a substrate, and other portions of a footwear apparatus are described later.

As illustrated in FIG. 1, first reservoirs 102 and second reservoirs 104 may have substantially circular, solid shapes (e.g., when viewed from above, as shown). In other embodiments, either or both of first and second reservoirs may have alternative shapes, including but not limited to square, rectangular, elliptical, hexagonal, substantially linear, substantially planar, spiral, disc-like, open-centered, cross, letters, numbers, symbols, irregular shapes, and/or other shapes.

In an embodiment, first reservoirs 102 may have diameters 108 (or widths) in a range of approximately 0.5 millimeters (mm) to 4 mm (approximately 2 mm in a particular embodiment), and second reservoirs 104 may have diameters 110 (or widths) in a range of approximately 0.5 mm to 4 mm (approximately 1 mm in a particular embodiment). In other embodiments, either or both first reservoirs 102 and/or second reservoirs 104 may have one or more dimensions (e.g., height, diameter, width, length) that are greater or smaller than the above-given range values. Reservoirs dimensions may, in various embodiments, be significantly larger or smaller than the above-given values. For example, an apparatus may include "nano-reservoirs," which may have dimensions measurable on a nanometer (nm) scale (e.g., from approximately 1 nm to approximately 10,000 nm or more).

Further, first reservoirs 102 and second reservoirs 104 may be of a similar size and shape, or their sizes and/or shapes may be substantially different from each other.

The material concentrations or quantities within and/or the relative sizes (e.g., dimensions or surface area) of the first and second reservoirs may be selected deliberately to achieve various characteristics of the apparatus' operational behavior. For example, the quantities of material within a first and second reservoir may be selected to provide an apparatus having an operational behavior that depletes at approximately a desired rate and/or that "dies" after an approximate period of time after activation. In an embodiment, the one or more first reservoirs and the one or more second reservoirs are configured to sustain one or more currents for an approximate pre-determined period of time, after activation. It is to be understood, however, that the amount of time that currents are sustained may depend on external conditions and factors (e.g., the quantity and type of activation material), and currents may occur intermittently depending on the presence or absence of activation material.

In various embodiments, materials within the first reservoirs and/or the second reservoirs may gradually deplete, after activation of the apparatus. For example, in an embodiment, a first reservoir may include silver and a second reservoir may include zinc. After activation of the apparatus, some or all of the silver and/or the zinc may gradually be expelled from its respective reservoir via electromotive force (e.g., iontophoresis), reservoir degradation, dissipation of the reservoir material, or otherwise. Alternatively or in addition, a voltage potential between the first and second reservoir may gradually decrease to near zero. When at least one of the galvanic materials has been depleted and/or the potential decreases significantly, reduction-oxidation (or "redox") reactions between the first and second reservoirs may eventually diminish and cease.

Certain reservoir materials may have therapeutic effects on the target tissue, and/or may result in other biologic activity, as will be described later. In some cases, it may be desirable to maintain therapeutic or other effects of one or more reservoir materials even after cessation of redox reactions between dissimilar reservoirs. Accordingly, a relative size of or material concentration within a first reservoir with respect to a second, dissimilar reservoir, may be selected so that the effects of the materials within the first reservoir continue beyond cessation of redox reactions. For example, a first reservoir may contain an amount of zinc and a second reservoir may contain an amount of silver. The amount of silver may be selected so that the silver is not completely depleted when redox reactions between the reservoirs have ceased, and accordingly therapeutic effects of the silver (e.g., anti-microbial effects) may continue. The reverse may also be the case (e.g., the zinc may not be completely depleted when the redox reactions have ceased).

In an embodiment, substrate 106 includes a top surface 112. Selected ones of the multiple first discrete reservoirs 102 are physically separated, across surface 112 of substrate 106, from selected ones of the multiple second discrete reservoirs 104, in an embodiment. Substrate 106 may form part of a substantially two-dimensional apparatus (e.g., an apparatus having width and height dimensions that are significantly greater than a depth dimension) or may form part of a substantially three-dimensional apparatus (e.g., an apparatus having width and height dimensions that are not significantly greater than a depth dimension), in various embodiments. In various embodiments, surface 112 may be substantially planar (e.g., flat). In other embodiments, substrate 106 may include a contoured and/or non-planar top surface. Substrate 106 and/or surface 112 may be rigid, or they may be moldable, bendable, and/or substantially conformable, in various embodiments.

In an embodiment, first discrete reservoirs 102 include first discrete reservoir surfaces "proximate to" top surface 112, and second discrete reservoirs 104 include second discrete reservoir surfaces proximate to top surface 112. The term "proximate to a surface" may be defined, in some embodiments, as having a positional relationship with respect to a surface, including positions above or slightly above, on, substantially flush with, below, or slightly below the surface. The term "proximate to a surface" may be defined, in other embodiments, as being located with respect to a surface so that electrical communication and/or ionic communication may be possible, for example, between dissimilar reservoirs. For example, but not by way of limitation, either or both of the first and second discrete reservoir surfaces may have a dome-like or puck-like shape, which extends above top surface 112. Alternatively, for example, but not by way of limitation, either or both of the first and second discrete reservoir surfaces may be exposed below the top surface 112 in depressions, holes or other openings.

Top surface 112 may be referred to herein as an "active surface." The term "active surface" may be defined, in some embodiments, as a substrate surface proximate to which electrical currents may be generated between dissimilar reservoirs in the presence of an electrically conductive material between the reservoirs. The term "current" includes a flow of charge per unit time (e.g., $I=dQ/dt$, where I is current, Q is charge, and t is time).

An active surface may or may not be a "tissue contacting surface," in various embodiments. A "tissue contacting surface" may be defined, in some embodiments, as a material surface, which during use, contacts an area of target tissue. For example, in an embodiment, top surface 112 may directly contact an area of target tissue during use of the apparatus, and accordingly, top surface 112 may function as both an active surface and a tissue contacting surface. In another embodiment, one or more additional materials may be included above top surface 112, and during use of the apparatus, a surface of one or more of the additional materials may function as a tissue contacting surface. Accordingly, in such an embodiment, the active surface and the tissue contacting surface may be different surfaces. A tissue contacting surface may include, for example but not by way of limitation, a layer of material and/or a solid, semi-solid, plastic, elastic, liquid, or gaseous conductive material. An active surface also may produce effects through one or more intermediate layers between the active surface and the target tissue (e.g., a sock or other layer).

The multiple first reservoirs 102 may form a portion of a first reservoir pattern, and the multiple second reservoirs 104 may form a portion of a second reservoir pattern, in an embodiment. In various embodiments, the term "pattern" means a collection of items (e.g., reservoirs) having a repetitious arrangement. In various embodiments, the term "pattern" means multiple copies of an arrangement of one or more items,(e.g., reservoirs), which is repeated across a surface.

The terms "reservoir pattern" and "pattern of reservoirs" may be used interchangeably herein, and have the same meaning or meanings. In various embodiments, the term "reservoir pattern" means a set of multiple reservoirs of a substantially similar type. In various embodiments, the term "reservoir pattern" means multiple reservoirs of a substantially similar type, which are arranged in spaced relation, co-planar spaced relation, spaced apart relation, and/or co-planar spaced apart relation with respect to each other. In various embodiments, the term "reservoir pattern" means a substantially repeating arrangement of reservoirs. In various embodiments, the term "reservoir pattern" means multiple sets of substantially similar reservoirs arranged across a planar surface. In an embodiment, the reservoirs in a set are arranged in a particular spaced relation with respect to other reservoirs in the set.

A first reservoir pattern may be interleaved with a second reservoir pattern, in various embodiments, where the first reservoir pattern includes one or more reservoirs of a first type, and the second reservoir pattern includes one or more reservoirs of a second type, which is dissimilar to the first type. In various embodiments, the term "interleaved" means that reservoirs of a first reservoir pattern are arranged in alternating positions, across a surface, with respect to reservoirs of a second reservoir pattern. The alternation of the first and second reservoirs may be 1:1, or other alternation ratios may be present. For example, but not by way of limitation, traveling along a line from a first point on the surface of a substrate to a second point on the surface, the alternation of reservoirs may be from a first reservoir to a second reservoir to a first reservoir to a second reservoir, and so on (i.e., a 1:1 alternation ratio). As another example, but not by way of limitation, the alternation of reservoirs along a line may be from a first reservoir to a second reservoir to a second reservoir to a first reservoir to a second reservoir to a second reservoir, and so on (i.e., a 1:2 alternation ratio). In addition, for a given embodiment, the alternation ratio along one line may be different from or the same as the alternation ratio along a different line.

In various embodiments, the term "interleaved" means that, across a surface, at least a portion of a boundary of a first reservoir pattern is positioned within at least a portion of a boundary of a second reservoir pattern, such that one or more first reservoirs of the first reservoir pattern are adjacent to one or more second reservoirs of the second reservoir pattern. In various embodiments, the term "interleaved" means that multiple selected reservoirs of a first reservoir pattern each have one or more nearest adjacent neighbor reservoirs, where a nearest adjacent neighbor reservoir is a reservoir of a second reservoir pattern. In various embodiments, the term "interleaved" means that selected reservoirs of a first reservoir pattern each are at least partially surrounded by reservoirs of a second reservoir pattern, and vice versa.

Either or both the first reservoir pattern and the second reservoir pattern may be consistent across a surface of substrate 106, as shown, or may have varying pattern densities. A pattern "density" may be defined, in some embodiments, as the number of reservoirs present per unit surface area. For example, but not by way of limitation, an apparatus may have variable pattern density (e.g., one or more relatively high pattern density areas and/or low pattern density areas). In FIG. 1, a pattern of twenty-one first reservoirs 102 and twenty-one second reservoirs 104 are illustrated. In alternative embodiments, more or fewer first and/or second reservoirs may be included in an apparatus.

In an embodiment, a first discrete reservoir 102 may be "adjacent to" one or more second discrete reservoirs 104, and vice versa. "Adjacent" reservoirs may be defined, in some embodiments, as dissimilar reservoirs, which are in physical proximity to each other such that, in the presence of an electrically conductive material between and in contact with the dissimilar reservoirs, an electrical current may be produced between the reservoirs. For example, in a subset 120 of reservoirs shown in FIG. 1, reservoirs 111, 112, 113 and 114 may be considered adjacent to reservoir 116. Other reservoirs beyond subset 120 also may be considered adjacent to reservoir 116, based on the above definition of "adjacent." "Adjacent" reservoirs may be defined, in various embodiments, as a set of selected reservoirs capable of creating, contributing or having electrical communication and/or ionic communication.

Substantially uniform or varying lateral spacings 130 may exist between the perimeters of adjacent reservoirs (e.g., reservoirs 111 and 116). In various embodiments, spacings 130 may be in a range of approximately 0.5 mm to 2.0 mm. In other embodiments, spacings 130 may be larger or smaller than the above-given range values. Lateral spacings 130 may be, in various embodiments, significantly smaller than the above-given values. For example, an apparatus may include very small reservoirs (e.g., "nano-reservoirs"). In such embodiments, lateral spacings 130 may be in a range from approximately 1 nm to approximately 10,000 nm or more. In an embodiment, the physical separation between adjacent dissimilar reservoirs provides for substantial electrical isolation between the adjacent dissimilar reservoirs, absent an electrically conductive material provided between them.

In various embodiments, selected ones of the multiple first discrete reservoirs 102 include a reducing agent, and selected ones of the multiple second discrete reservoirs 104 include an oxidizing agent, or vice versa. In the presence of an electrically conductive material between the first reservoirs and the second reservoirs, redox reactions may be produced between the first and second reservoirs. Although the electrically conductive material may physically contact the reservoirs to facilitate redox reactions, it may be that the redox reactions occur when the conductive material does not physically contact the reservoirs.

Selected ones of the second reservoir surfaces may be positioned in spaced relation to selected ones of the first reservoir surfaces to produce redox reactions between the surfaces, in the presence of an electrically conductive material facilitating electrical and/or ionic communication between the second reservoir surfaces and the first reservoir surfaces. In an embodiment, the redox reactions may occur spontaneously when a conductive material is brought in proximity to first and second dissimilar reservoirs, such that the conductive material provides a medium for electrical communication and/or ionic communication between the first and second dissimilar reservoirs. In other words, in an embodiment, electrical currents may be produced between first and second dissimilar reservoirs without the use of an external battery or other power source (e.g., a direct current (DC) or an alternating current (AC) power source). Accordingly, in various embodiments, an apparatus is provided, which is "electrically self contained," and yet the apparatus may be activated to produce electrical currents. The term "electrically self contained" may be defined, in some embodiments, as being capable of producing electricity (e.g., producing currents) without an external battery or power source. In other embodiments, an apparatus may be provided which includes an external battery or power source.

The terms "reduction-oxidation reaction" or "redox reaction" may be defined, in some embodiments, as a reaction involving the transfer of one or more electrons from a reducing agent to an oxidizing agent. The term "reducing agent" may be defined, in some embodiments, as a reactant in a redox reaction, which donates electrons to a reduced species. A "reducing agent" is thereby oxidized in the reaction. The term "oxidizing agent" may be defined, in some embodiments, as a reactant in a redox reaction, which accepts electrons from the oxidized species. An "oxidizing agent" is thereby reduced in the reaction. In various embodiments, a redox reaction produced between a first and second reservoir provides a current between the dissimilar reservoirs.

Figure 2:
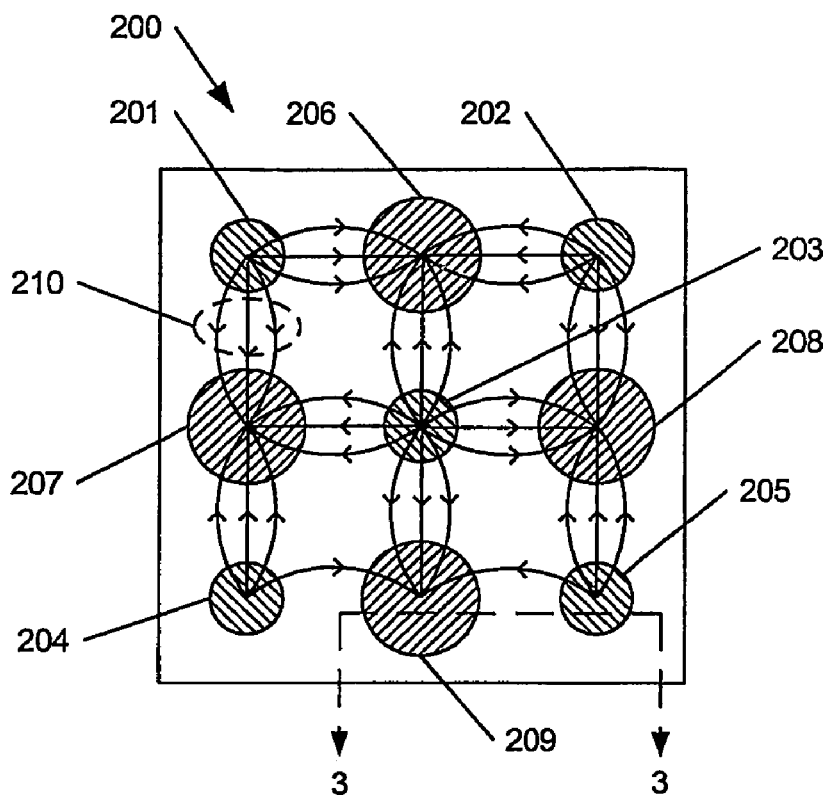
FIG. 2 is a top view of a portion of a footwear apparatus, illustrating current flow between dissimilar reservoirs, in accordance with an example embodiment.

FIG. 2 is a top view of a portion of a footwear apparatus 200, illustrating current flow between dissimilar reservoirs, in accordance with an example embodiment. First reservoirs 201, 202, 203, 204, and 205 may include one or more oxidizing agents, and second reservoirs 206, 207, 208, and 209 may include one or more reducing agents, or vice versa. An electrically conductive material (not illustrated) may be dispersed between some or all of the first reservoirs 201-205 and the second reservoirs 206-209. In the presence of an electrically conductive material between adjacent dissimilar reservoirs, redox reactions may take place, and thus currents may be produced between the adjacent dissimilar reservoirs. Current flows 210 are indicated by arrows between reservoirs 201-205 and reservoirs 206-209. As FIG. 2 illustrates, currents 210 may be produced between each set of adjacent first reservoirs 201-205 and second reservoirs 206-209, in the presence of a conductive material. Accordingly, a field of multiple currents 210 may be produced across a surface of a substrate, creating a planar surface current that includes multiple subcurrents. A current 210 between a set of two adjacent, dissimilar reservoirs may be referred to herein as a "single-cell current," and an aggregate of multiple currents 210 between multiple sets of adjacent, dissimilar reservoirs may be referred to herein as a "multiple-cell current." Accordingly, some embodiments may provide, in the presence of an electrically conductive material, a substantially planar matrix or multiplicity of electrically active cells, wherein a cell includes a first reservoir and a second reservoir (i.e., adjacent dissimilar reservoirs), and any given reservoir may form a portion of one or more cells. In some embodiments, the first and second reservoirs may be of a structure, orientation, and composition to produce current levels within cells, which may approximate current levels that may naturally be produced by a human or animal and present in an area of healthy healing tissue. Currents 210 may be substantially uniform across an active surface, or a varying current density may be present across an active surface.

Each set of adjacent, dissimilar reservoirs (e.g., reservoirs 201 and 206) may form a "galvanic cell," in an embodiment. When a particular reservoir is adjacent to multiple dissimilar reservoirs, then the particular reservoir may form portions of multiple galvanic cells. For example, reservoir 203 may form portions of four or more galvanic cells (e.g., cell A includes reservoirs 203 and 206, cell B includes reservoirs 203 and 207, cell C includes reservoirs 203 and 208, and cell D includes reservoirs 203 and 209).

A "galvanic cell" may be defined, in some embodiments, as an electrochemical cell with a positive cell potential, which may allow chemical energy to be converted into electrical energy. More particularly, a galvanic cell may include a first reservoir serving as an anode and a second, dissimilar reservoir serving as a cathode. Each galvanic cell may store energy in the form of chemical potential energy. When a conductive material is located proximate to a cell such that the material may provide electrical and/or ionic communication between the cell elements, the chemical potential energy may be released as electrical energy. Accordingly, each set of adjacent, dissimilar reservoirs may function as a single-cell battery, and the distribution of multiple sets of adjacent, dissimilar reservoirs within the apparatus may function as a field of single-cell batteries, which in the aggregate forms a multiple-cell battery distributed across a surface.

When a first reservoir includes a reducing agent, and a second reservoir includes an oxidizing agent, or vice versa, a potential difference may exist between the first reservoir and the second reservoir. In a first state, an apparatus is electrically quiescent (e.g., current flow between reservoirs is substantially zero). In an embodiment, an apparatus may be "activated" when a conductive material is brought into proximity with the first reservoir and the second reservoir, enabling a current flow to occur between the reservoirs, via electrical communication and/or ionic communication. Such a conductive material may be referred to herein as an "activation material." A magnitude of the current, I, substantially is a function of the potential difference, V, between the reservoirs, and the conductance or resistance, R, of the conductive material. In other words, the current I between the reservoirs approximately equals the voltage potential, V, between reservoirs divided by the resistance, R, of the conductive material, or I=V/R.

Said another way, the magnitudes of currents 210 producible between adjacent, dissimilar reservoirs may be affected by one or more factors, including but not limited to, the distance between adjacent dissimilar reservoirs, the potential difference between the reservoirs (e.g., the quantity of electrons that a reducing agent may have available to donate to an oxidizing agent, the quantity of electrons that an oxidizing agent may be able to accept), resistance of the conductive material, and other factors. In addition, a current between reservoirs may change as a function of time, as the above factors change. Voltage potential differences in a range from approximately 0.05 Volts (V) to approximately 5.0 V may be present between dissimilar reservoirs, in an embodiment. In other embodiments, higher and/or lower voltage differences between dissimilar reservoirs may be present. Further, currents in a range from approximately 1 microampere (mA) to approximately 100 mA may be producible between dissimilar reservoirs, in an embodiment. In other embodiments, higher and/or lower currents may be producible. Currents may be affected by the resistance of the conductive material present between reservoirs. Resistances of conductive materials may vary significantly from near zero resistance to near infinite resistance.

When an apparatus is applied to an area of tissue and activated (or activated and then applied), a total current, $I_{TOTAL}$, between dissimilar reservoirs may be described as $I_{TISSUE} + I_{(CONDUCTIVE\ MATERIAL)}$. When the resistance of the tissue is greater than the resistance of the conductive material, then proportionally more current may flow through the conductive material than through the tissue. Accordingly, in various embodiments, a conductive material may be selected, which has a resistance that may be greater or less than the anticipated resistance of a type of target tissue, depending on whether more or less current is desired to flow through the target tissue.

In various embodiments, an apparatus may be used to apply electricity to tissue (e.g., skin or other tissue) in need of treatment. The electricity may be generated by a first reservoir (e.g., a first conductive electrode) in electrical communication with a second, dissimilar reservoir (e.g., a second conductive electrode), and the first reservoir and the second reservoir may be in ionic communication with the tissue. The term "electrical communication" may be defined, in some embodiments, as passage of electrons between elements (e.g., first and second reservoirs) through direct contact and/or through one or more conductive materials. The term "ionic communication" may be defined, in some embodiments, as passage of electrons between elements (e.g., first and second reservoirs, a conductive material, and/or tissue) through migration of ions as "electron movers" in contact with the elements (e.g., electrons may pass between a reservoir and tissue via ionic transport of electrolytes in contact with a reservoir and the tissue).

In various embodiments, the difference of the standard potentials of the first and second reservoirs may be in a range from 0.05 V to approximately 5.0 V. In a particular embodiment, the difference of the standard potentials of the first and second reservoirs may be at least 0.2 V. In embodiments that include very small reservoirs (e.g., on the nanometer scale), the difference of the standard potentials may be substantially less. The electrons that pass between the first reservoir and the second reservoir may be generated as a result of the difference of the standard potentials.

Figure 3:
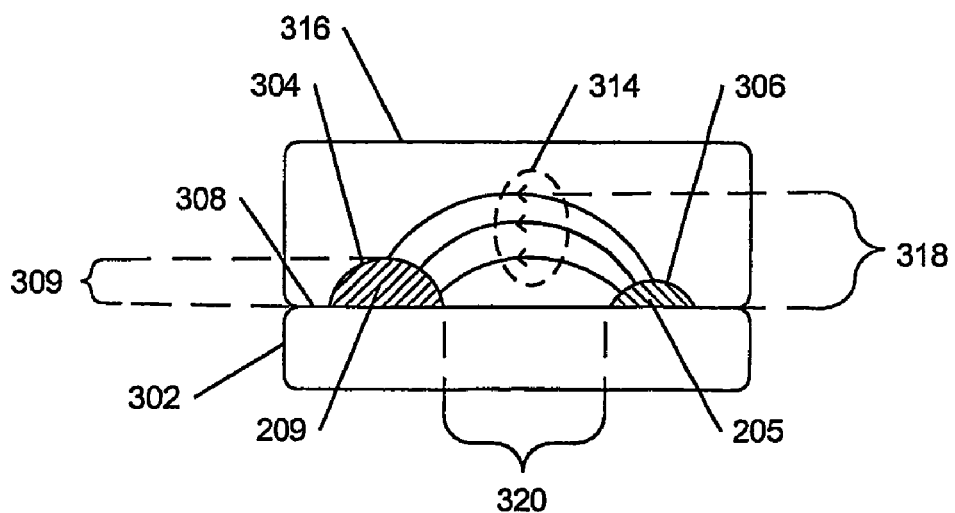
FIG. 3 is a cross-sectional, side view of a portion of the footwear apparatus of FIG. 2 along section line 3-3, in accordance with an example embodiment.

FIG. 3 is a cross-sectional, side view of a portion of the footwear apparatus of FIG. 2 along lines 3-3, in accordance with an example embodiment. The illustrated portion includes a first reservoir 209 and a second reservoir 205 joined with a substrate 302. In the illustrated embodiment, a first reservoir surface 304 and a second reservoir surface 306 extend above a top surface 308 of substrate 302. In other embodiments, either or both reservoir surfaces 304, 306 may be substantially flush with top surface 308 and/or below top surface 308. Further, in the illustrated embodiment, first reservoir surface 304 and second reservoir surface 306 are shown to have a rounded or dome-like shape. In other embodiments, the shape of either or both reservoir surfaces 304, 306 may be substantially flat, disk-like, cylindrical, conical, concave, or otherwise shaped.

In an embodiment, a reservoir may have a height or thickness (e.g., height 309) in a range from approximately 1000 Angstroms to approximately 5 millimeters. In other embodiments, a reservoir may have a height or thickness that is greater than or smaller than the above-given range. In particular embodiments, reservoirs may be "post-like" structures (e.g., protrusions 2406, FIG. 24), which are significantly higher than 5 millimeters.

In an embodiment, a current 314 may be produced when a conductive material 316 (e.g., an activation material) is brought into proximity to all or portions of both the first reservoir surface 304 and the second reservoir surface 306, thus enabling electrical communication and/or ionic communication between the surfaces 304, 306. The conductive material 316 may include, but is not limited to, one or more liquid, solid, semi-solid, or gaseous materials, as will be described in more detail later.

In an embodiment, a current 314 may penetrate into the conductive material 316 by a penetration height 318 above the top surface 308 of the substrate. Accordingly, in certain circumstances, current 314 may penetrate into an area of target tissue.

The penetration height 318 of a current may be a function of one or more of various factors, including but not limited to, the spacing 320 between reservoir surfaces 304, 306 and other factors. Penetration heights 318 may be substantially uniform across an active surface, or may vary. Currents having penetration heights in a range from approximately 0.05 mm to approximately 2.0 mm are producible, in an embodiment. In other embodiments, currents having higher and/or lower penetration heights may be producible.

In various embodiments, a reservoir may be formed from a single material or a relatively homogenous combination of materials. In other embodiments, a reservoir may be formed from two or more material compositions. Such a reservoir may be referred to herein as a "composite" reservoir.

Figure 4:
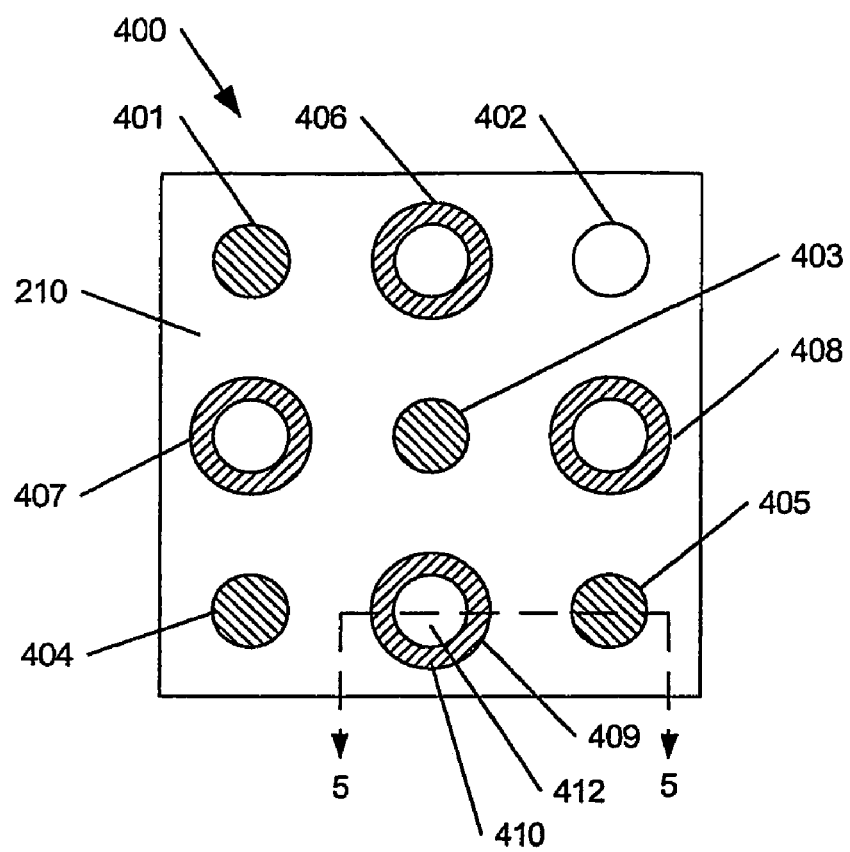
FIG. 4 is a top view of a portion of a footwear apparatus, which includes at least one composite reservoir, in accordance with an example embodiment.

FIG. 4 is a top view of a portion of a footwear apparatus 400, which includes at least one "composite" reservoir, in accordance with an example embodiment. First reservoirs 401, 402, 403, 404, and 405 may function as first portions of galvanic cells, and second reservoirs 406, 407, 408, and 409 may function as second portions of galvanic cells. An electrically conductive material (e.g., an activation material, not illustrated) may be dispersed between some or all of the first reservoirs 401-405 and the second reservoirs 406-409, providing for the production of currents between the first and second reservoirs.

In an embodiment, selected ones of first and/or second reservoirs may be formed from two or more material compositions. For purposes of example, a composite reservoir 409 is shown as being formed from a first composition 410 and a second composition 412. Although certain reservoirs in FIG. 4 are illustrated as being composite reservoirs, it is to be understood that other reservoirs also or alternatively could be composite reservoirs.

First composition 410, in an embodiment, may form a peripheral or outer portion of reservoir 409, and second composition 412 may form an interior or central portion of reservoir 409. In alternative embodiments, a first composition and a second composition may be alternatively arranged, with respect to each other. For example, but not by way of limitation, a first and second composition may be adjacent to each other, layered such that they form a multiple-layer (e.g., two or more), stacked reservoir, or otherwise combined together.

Figure 5:
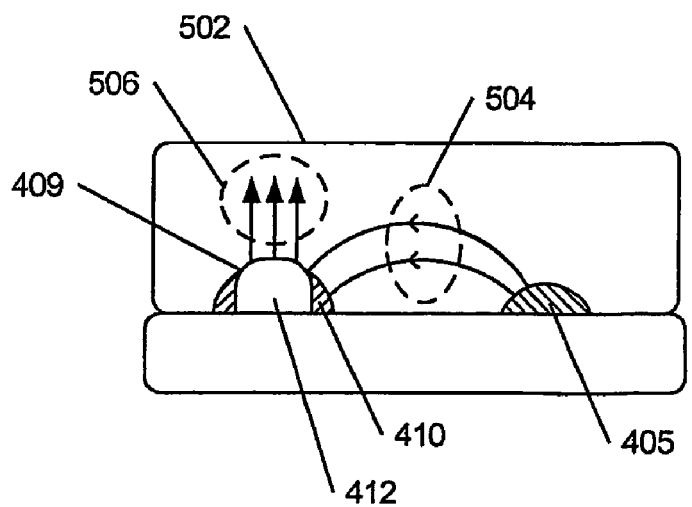
FIG. 5 is a cross-sectional, side view of a portion of the footwear apparatus of FIG. 4 along section line 5-5, in accordance with an example embodiment.

FIG. 5 is a cross-sectional, side view of a portion of the footwear apparatus of FIG. 4 along lines 5-5, in accordance with an example embodiment. In an embodiment, reservoir 409 may function as a first portion of a galvanic cell, and reservoir 405 may form a second portion of the galvanic cell. More particularly, first composition 410 may include a reducing agent, and reservoir 405 may include an oxidizing agent, or vice versa. Accordingly, in the presence of a conductive material 502 between reservoir 405 and first composition 410, a current 504 may be produced between reservoir 405 and first composition 410.

In an embodiment, second composition 412 may include a material which disperses outward (e.g., by iontophoresis, dissolution, or otherwise) from reservoir 409, as indicated by arrows 506. Second composition 412 may, for example, include a material that produces a biological response when it contacts an area of target tissue. In alternative embodiments, first composition 410 and second combination 412 may be oppositely arranged. For example, but not by way of limitation, an inner portion of reservoir 409 may include a reducing (or oxidizing) agent, and an outer portion of reservoir 409 may include a material, which disperses outward from reservoir 409, or vice versa.

As discussed previously, multiple first discrete reservoirs and second, dissimilar discrete reservoirs may be arranged in interleaved patterns, in various embodiments. For example, referring again to FIG. 1, first discrete reservoirs 102 are arranged in rows, and each successive row is offset from the previous row by approximately one-half the distance between the first reservoirs 102. Second discrete reservoirs 104 are interleaved with the first discrete reservoirs 102, and are similarly arranged in rows. In addition, in FIG. 1, selected ones of the first discrete reservoirs 102 may be considered to be adjacent to four or more second discrete reservoirs 104, and vice versa. Accordingly, a correlation of approximately 1:1 may exist between the number of first discrete reservoirs 102 and the number of second discrete reservoirs 104. According to the above-described characteristics of footwear apparatus 100, interleaved patterns of first and second discrete reservoirs may be defined. In the illustrated embodiment, the patterns are uniformly distributed across the substrate surface. In other embodiments, non-uniform pattern distributions may be present.

In alternative embodiments, a footwear apparatus may be formed using other configurations of patterns and/or reservoir shapes. FIGS. 6-19 illustrate various alternative embodiments. The illustrated embodiments are not meant to limit the inventive subject matter or the scope of the claims only to the illustrated embodiments. Instead, other configurations of patterns and/or reservoir shapes are contemplated to fall within the scope of the inventive subject matter. In addition, certain cross-hatching is used to differentiate first reservoirs from second, dissimilar reservoirs. It is to be understood that the use of the cross-hatching is not intended to correlate the materials used within those reservoirs to either a reducing agent or an oxidizing agent, as they may have been correlated in the description associated with previously-described figures.

Figure 6:
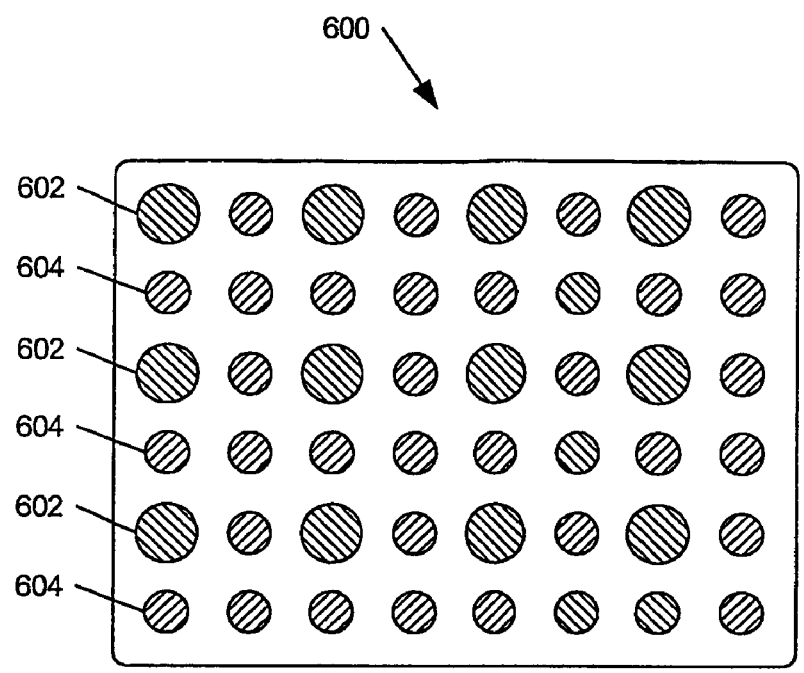
FIG. 6 is a top view of a portion of a footwear apparatus having a second configuration of dissimilar reservoirs, in accordance with an example embodiment.

FIG. 6 is a top view of a portion of a footwear apparatus 600 having a second configuration of dissimilar reservoirs, in accordance with an example embodiment. Footwear apparatus 600 includes multiple first reservoirs 602 and multiple second, dissimilar reservoirs 604. In the illustrated embodiment, selected ones of the first discrete reservoirs 602 may be considered to be adjacent to eight or more second discrete reservoirs 604. In addition, selected ones of the second discrete reservoirs 604 may be considered to be adjacent to four or more first discrete reservoirs 602. Accordingly, a number of first discrete reservoirs may be different from a number of second discrete reservoirs (e.g., the correlation between numbers of first and second discrete reservoirs may be substantially different from a 1:1 correlation).

Figure 7:
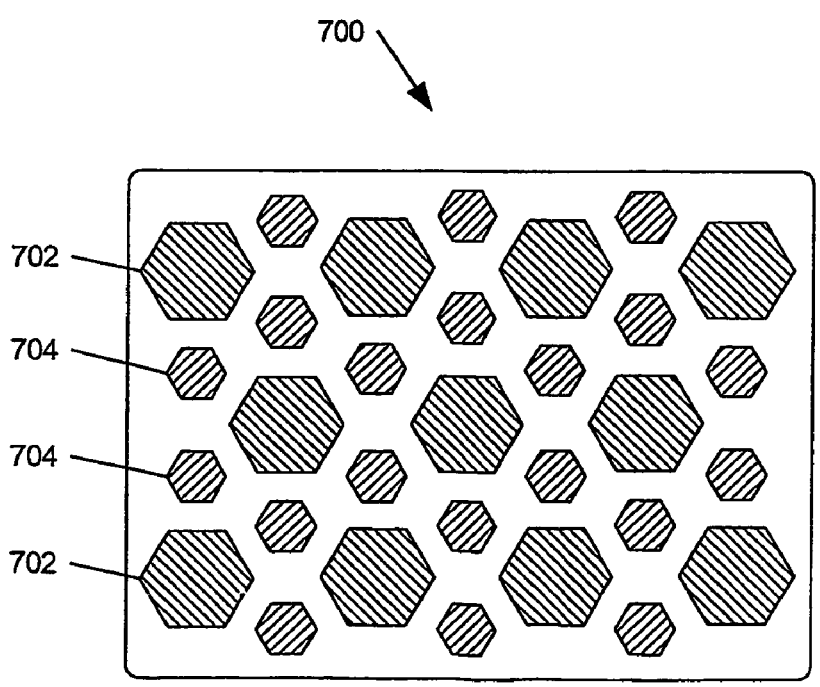
FIG. 7 is a top view of a portion of a footwear apparatus having a third configuration of dissimilar reservoirs, in accordance with an example embodiment.

FIG. 7 is a top view of a portion of a footwear apparatus 700 having a third configuration of dissimilar reservoirs, in accordance with an example embodiment. Footwear apparatus 700 includes multiple first reservoirs 702 and multiple second, dissimilar reservoirs 704. In the illustrated embodiment, selected ones of the first discrete reservoirs 702 may be considered to be adjacent to six or more second discrete reservoirs 704. In addition, selected ones of the second discrete reservoirs 704 may be considered to be adjacent to three or more first discrete reservoirs 702.

Figure 8:
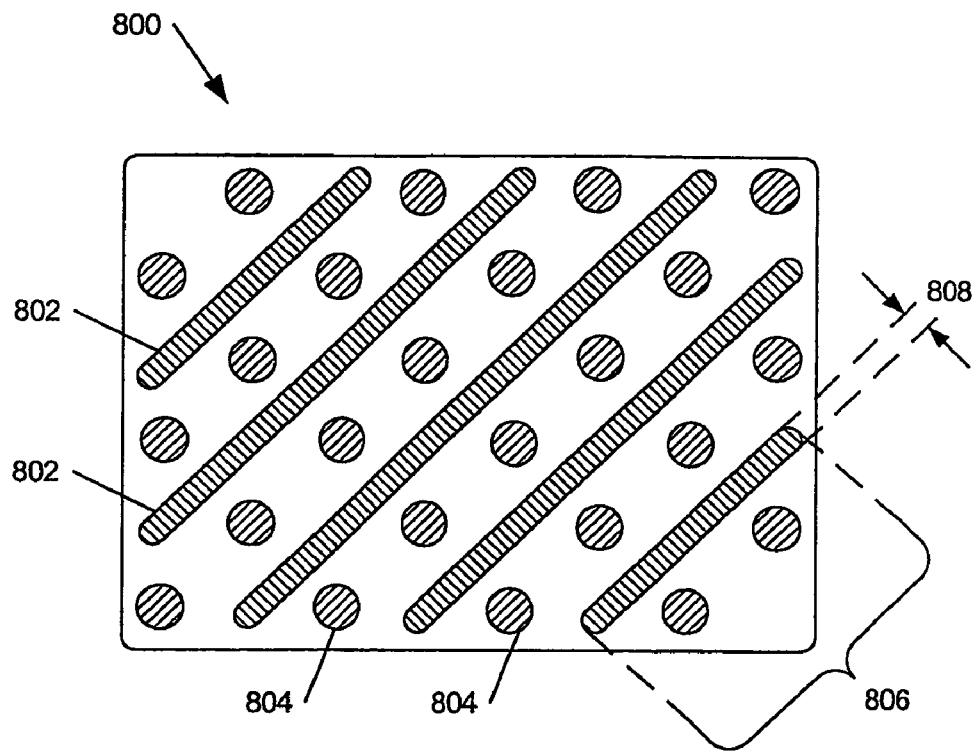
FIG. 8 is a top view of a portion of a footwear apparatus having a fourth configuration of dissimilar reservoirs, in accordance with an example embodiment.

FIG. 8 is a top view of a portion of a footwear apparatus 800 having a fourth configuration of dissimilar reservoirs, in accordance with an example embodiment. Footwear apparatus 800 includes multiple first reservoirs 802 and multiple second, dissimilar reservoirs 804. In the illustrated embodiment, selected ones of the first discrete reservoirs 802 are "substantially linear" in shape. The term "substantially linear" may be defined, in some embodiments, as including shapes having a length 806, which is greater than a width 808 by a factor of at least approximately 2:1. A "substantially linear" shape may be substantially straight, or may be curved, coiled or undulating. In the illustrated embodiment, multiple first reservoirs 802 are arranged in a spaced, substantially parallel arrangement to each other, and multiple second discrete reservoirs 804 are arranged in regions between the multiple first reservoirs 802.

Figure 9:
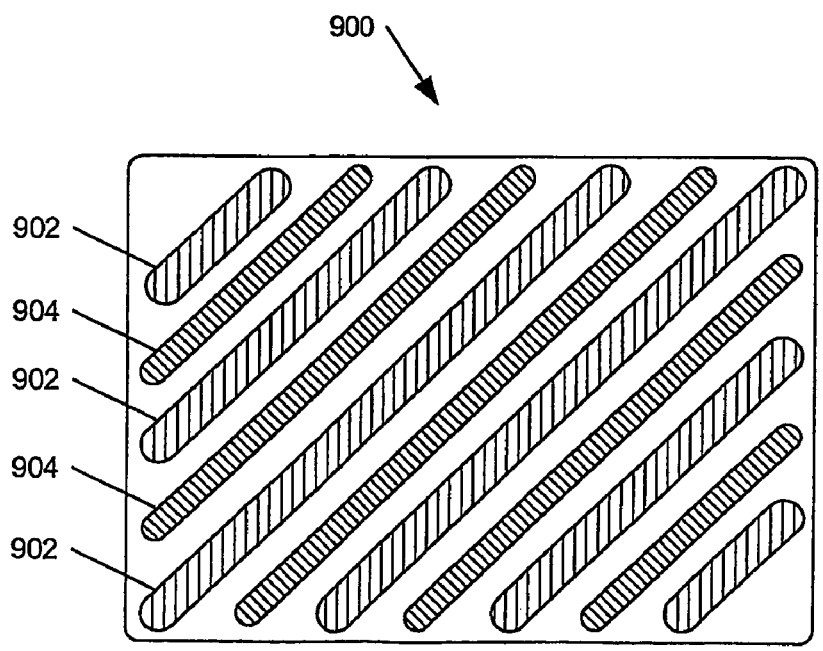
FIG. 9 is a top view of a portion of a footwear apparatus having a fifth configuration of dissimilar reservoirs, in accordance with an example embodiment.

FIG. 9 is a top view of a portion of a footwear apparatus 900 having a fifth configuration of dissimilar reservoirs, in accordance with an example embodiment. Footwear apparatus 900 includes multiple first reservoirs 902 and multiple second, dissimilar reservoirs 904. In the illustrated embodiment, selected ones of the first discrete reservoirs 902 and selected ones of the second discrete reservoirs 904 are substantially linear in shape. In the illustrated embodiment, multiple first reservoirs 902 are arranged in a spaced, substantially parallel arrangement to each other, and multiple second discrete reservoirs 904 are arranged in regions between the multiple first reservoirs 902, where the multiple second discrete reservoirs 904 are also arranged in a spaced, substantially parallel arrangement to each other.

Figure 10:
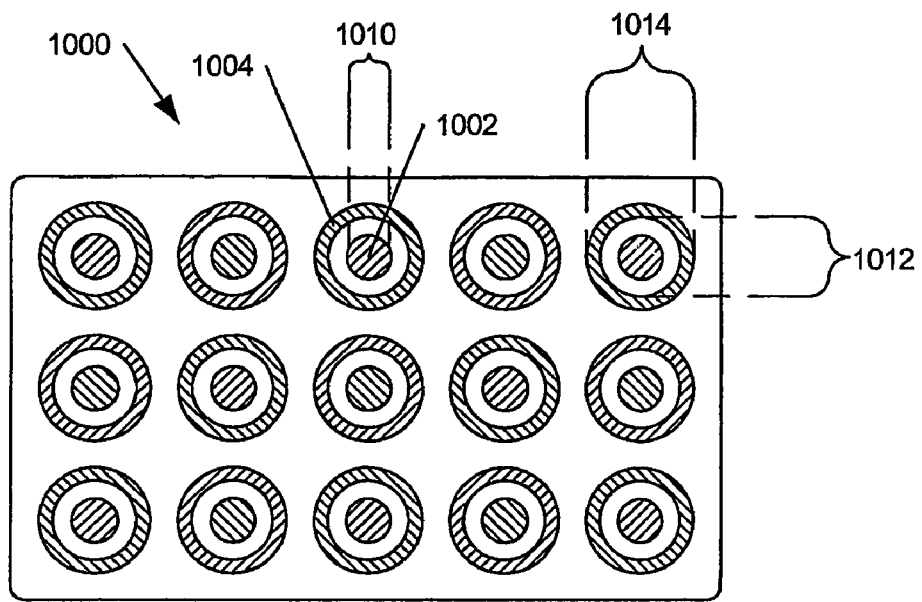
FIG. 10 is a top view of a portion of a footwear apparatus having a sixth configuration of dissimilar reservoirs, in accordance with an example embodiment.

FIG. 10 is a top view of a portion of a footwear apparatus 1000 having a sixth configuration of dissimilar reservoirs, in accordance with an example embodiment. Footwear apparatus 1000 includes multiple first reservoirs 1002 and multiple second, dissimilar reservoirs 1004, forming multiple galvanic cells. In the illustrated embodiment, a first discrete reservoir 1002 and a second discrete reservoir 1004 are concentrically arranged, with respect to each other, forming a "concentric" galvanic cell. A first discrete reservoir 1002 is shown as having a circular shape of a first diameter 1010, and a second discrete reservoir 1004 is shown as having a ring shape having an interior diameter 1012 and an exterior diameter 1014. In an embodiment, the interior diameter 1012 of the second discrete reservoir 1004 is larger than the first diameter 1010 of the first discrete reservoir 1002, forming a spacing between the reservoirs. Accordingly, the second discrete reservoir 1004 is concentric with and physically separated from the first discrete reservoir 1002, forming a first galvanic cell. In an embodiment, the materials for adjacent galvanic cells may be reversed, so that additional galvanic cells may be formed from adjacent sets of first and second discrete reservoirs. Alternatively, the materials for adjacent, concentric galvanic cells may be consistently selected.

Figure 11:
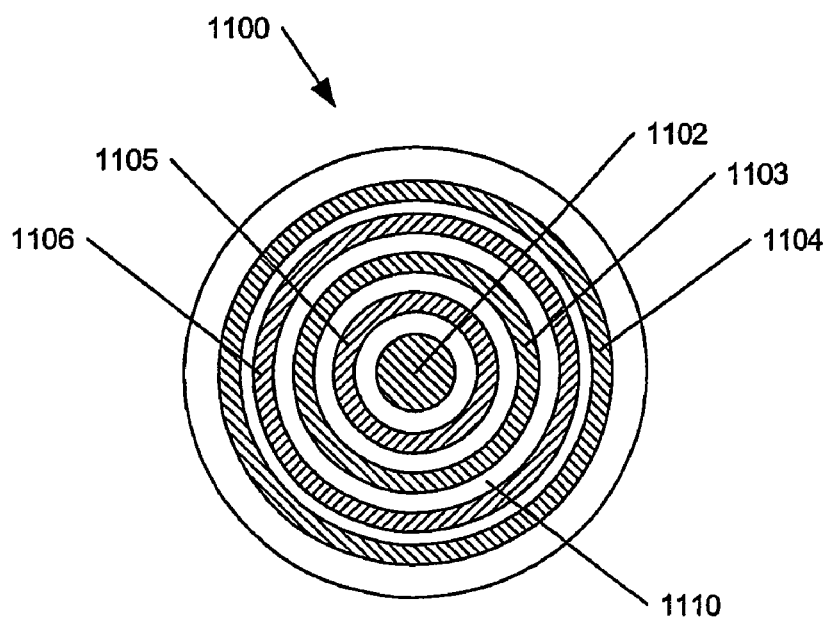
FIG. 11 is a top view of a portion of a footwear apparatus having a seventh configuration of dissimilar reservoirs, in accordance with an example embodiment.

FIG. 11 is a top view of a portion of a footwear apparatus 1100 having a seventh configuration of dissimilar reservoirs, in accordance with an example embodiment. Footwear apparatus 1100 includes multiple first reservoirs 1102, 1103, 1104 and multiple second, dissimilar reservoirs 1105, 1106. In the illustrated embodiment, selected ones of reservoirs 1102-1106 may be concentrically arranged, with respect to each other. Spacings 110 may exist between reservoirs 1102-1106 to provide for electrical isolation between adjacent reservoirs, in the absence of a conductive material between the reservoirs.

Embodiments previously described include footwear apparatus having multiple first reservoirs and multiple second, dissimilar reservoirs. In other embodiments, a footwear apparatus may include a single first reservoir and multiple second, dissimilar reservoirs.

Figure 12:
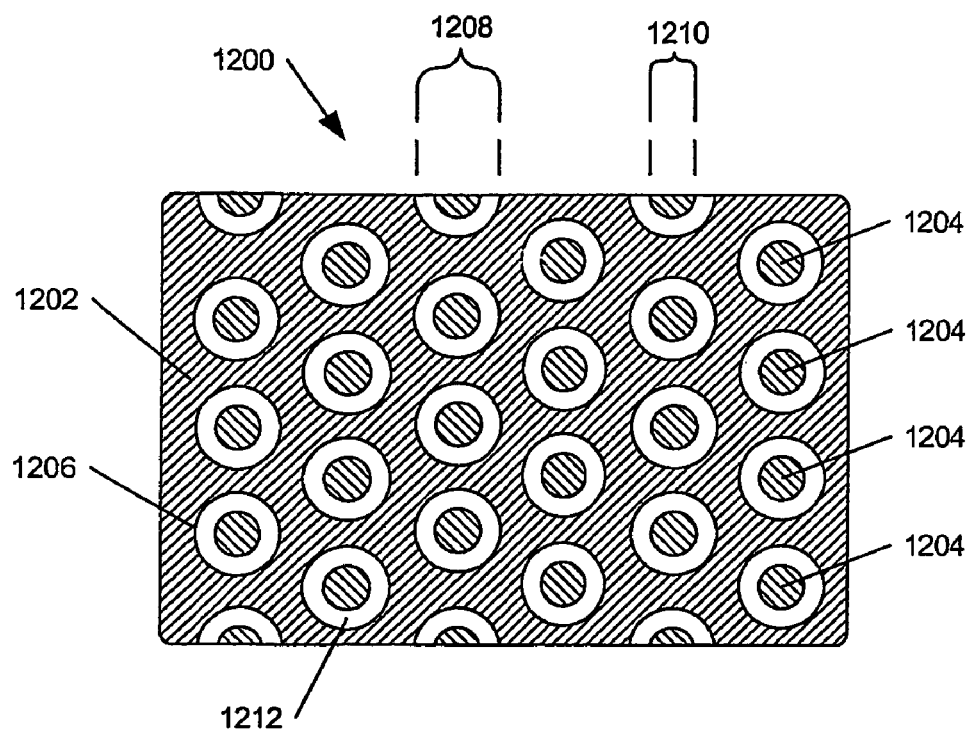
FIG. 12 is a top view of a portion of a footwear apparatus having an eighth configuration of dissimilar reservoirs, in accordance with an example embodiment.

FIG. 12 is a top view of a portion of a footwear apparatus 1200 having an eighth configuration of dissimilar reservoirs, in accordance with an example embodiment. Footwear apparatus 1200 includes a single first reservoir 1202 and multiple second, dissimilar reservoirs 1204. In the illustrated embodiment, first discrete reservoir 1202 is "substantially planar," with multiple openings 1206. The term "substantially planar" may be defined, in some embodiments, as including areas of material having a length and a width that are greater than a distance between two or more reservoirs of a first type. A "substantially planar" shape may be substantially flat and uninterrupted, or may have openings, divots, or other interruptions therein, and/or may be curved or bent. In an embodiment, openings 1206 have a diameter 1208 that is larger than a diameter 1210 of second discrete reservoirs 1204. Accordingly, spacings 1212 exist between the second discrete reservoirs 1204 and the first discrete reservoir 1202.

In still other embodiments, a footwear apparatus may include a single first discrete reservoir and a single second discrete reservoir. For example, but not by way of limitation, first and second discrete reservoirs may be coiled around each other, arranged in a tongue-in-groove, toothed or zig-zag configuration, or otherwise arranged to produce multiple currents across a surface, when a conductive material (e.g., an activation material) is provided between the first and second reservoirs.

In FIGS. 1-12, first discrete reservoirs are shown to be physically separated from second dissimilar reservoirs, thus achieving electrical isolation between the first and second reservoirs, in the absence of a conductive material between the reservoirs. In alternative embodiments, some or all of the dissimilar reservoirs may include areas or points of contact.

Figure 13:
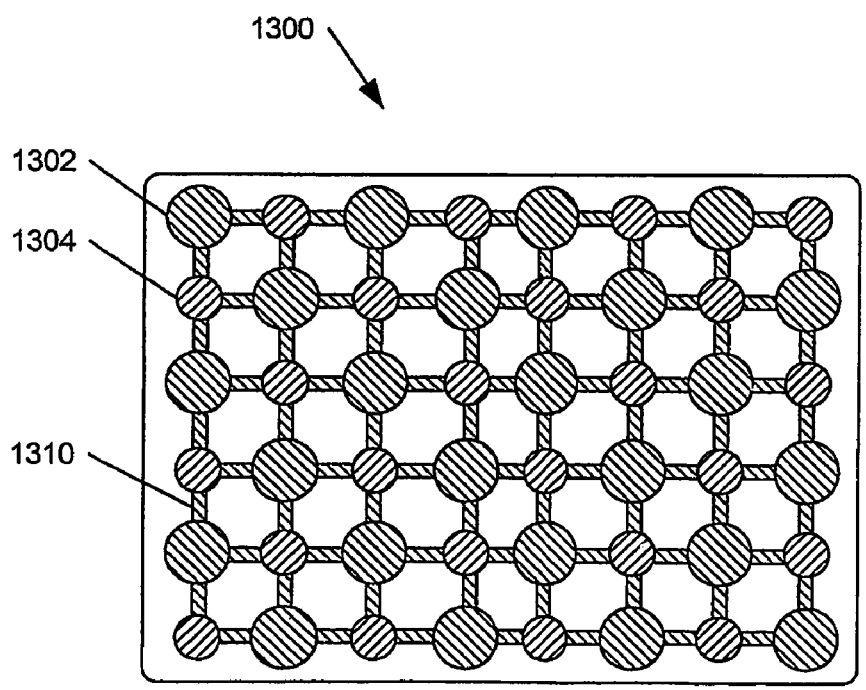
FIG. 13 is a top view of a portion of a footwear apparatus having an ninth configuration of dissimilar reservoirs, in accordance with an example embodiment.

FIG. 13 is a top view of a portion of a footwear apparatus 1300 having a ninth configuration of dissimilar reservoirs, in accordance with an example embodiment. Footwear apparatus 1300 includes multiple first reservoirs 1302 and multiple second, dissimilar reservoirs 1304. In addition, footwear apparatus 1300 includes connecting portions 1310, which may interconnect selected ones or substantially all of the first reservoirs 1302 and the second reservoirs 1304.

Figure 14:
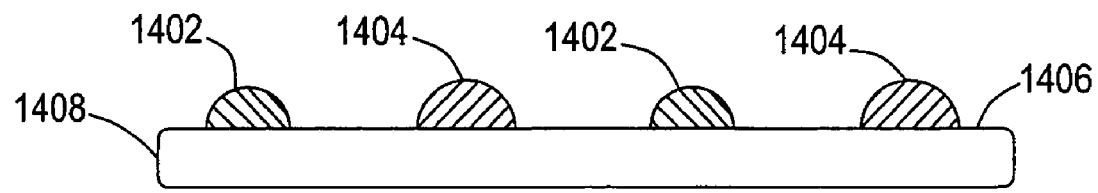
FIG. 14 is a cross-sectional, side view of a portion of a footwear apparatus having multiple first reservoirs and multiple second reservoirs joined to a surface of a substrate, in accordance with an example embodiment.

FIG. 14 is a cross-sectional, side view of a portion of a footwear apparatus having multiple first reservoirs 1402 and multiple second reservoirs 1404 joined to a surface 1406 of a substrate 1408, in accordance with an example embodiment. Substrate 1408 may be a single-layer substrate or a multiple-layer substrate, in various embodiments.

In various embodiments, first and/or second reservoirs 1402, 1404 may be joined to surface 1406 using any of several techniques. For example, but not by way of limitation, first and/or second reservoirs may be joined to surface 1406 using one or more techniques such as adhering reservoir materials onto surface 1406, painting or printing (e.g., screen printing or ink jet printing) reservoir material onto surface 1406, tattooing reservoir material onto surface 1406 and/or onto an area of target tissue, depositing reservoir material onto surface 1406 using a deposition process (e.g., chemical deposition, electrochemical deposition, vapor deposition, plating, spray coating, gravure coating, plasma coating, dip coating, nanometer scale deposition, vacuum deposition or sputtering), bonding or fusing reservoir material onto surface 1406, and or other ways of joining.

Figure 15:
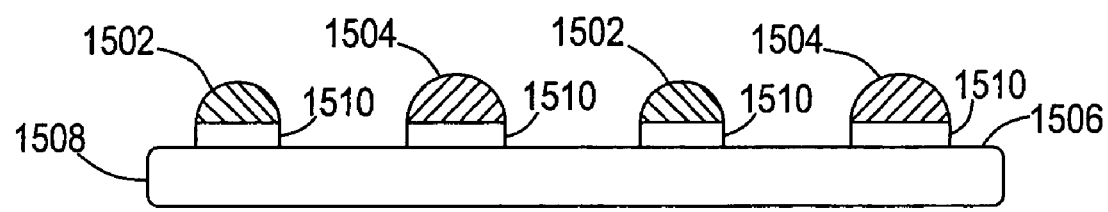
FIG. 15 is a cross-sectional, side view of a portion of a footwear apparatus having multiple first reservoirs and multiple second reservoirs adhered to a surface of a substrate, in accordance with an example embodiment.

FIG. 15 is a cross-sectional, side view of a portion of a footwear apparatus having multiple first reservoirs 1502 and multiple second reservoirs 1504 adhered to a surface 1506 of a substrate 1508 using an adhesive material 1510, in accordance with an example embodiment. In various embodiments, adhesive material 1510 may be deposited onto surface 1506 prior to or consecutively with adherence of the first and/or second reservoirs 1502, 1504. Adhesive material 1510 may be limited in distribution over the surface 1502, for example as shown in FIG. 15. In an alternative embodiment, adhesive material may be applied as a layer covering a substantial portion of surface 1502.

Figure 16:
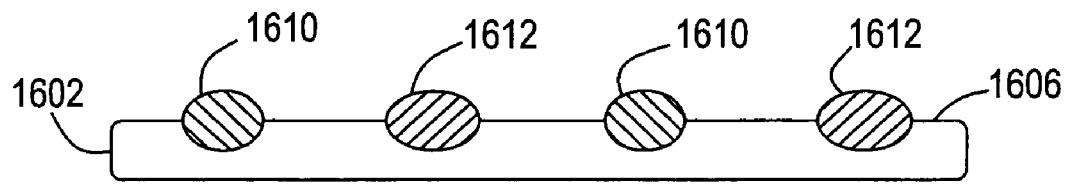
FIG. 16 is a cross-sectional, side view of a portion of a substrate having depressions in a surface, within which multiple first reservoirs and multiple second reservoirs are joined, in accordance with an example embodiment.

FIG. 16 is a cross-sectional, side view of a portion of a substrate 1602 having depressions in a surface 1606, within which multiple first reservoirs 1610 and multiple second reservoirs 1612 are joined, in accordance with an example embodiment. Depressions may be formed during manufacture of the substrate 1602 or later, in various embodiments.

Figure 17:
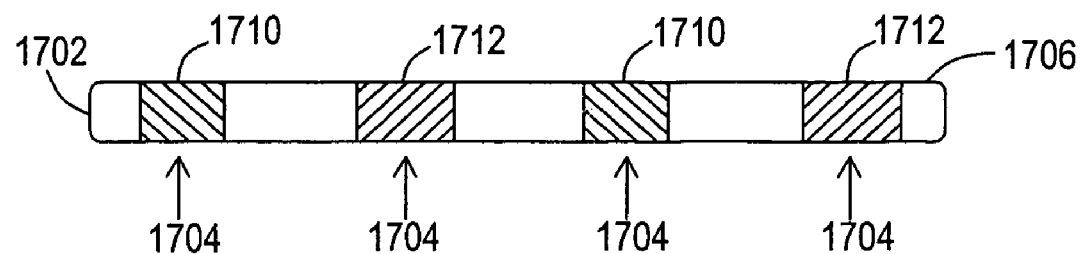
FIG. 17 is a cross-sectional, side view of a portion of a substrate having holes in a surface, within which multiple first reservoirs and multiple second reservoirs are deposited, in accordance with an example embodiment.

FIG. 17 is a cross-sectional, side view of a portion of a substrate 1702 having holes 1704 in a surface 1706, within which multiple first reservoirs 1710 and multiple second reservoirs 1712 are deposited, in accordance with an example embodiment. Holes 1704 may be formed during manufacture of the substrate 1702 or later, in various embodiments. Although holes 1704 are shown to extend completely through substrate 1702, one or more of the holes may extend only partially through the substrate.

Figure 18:
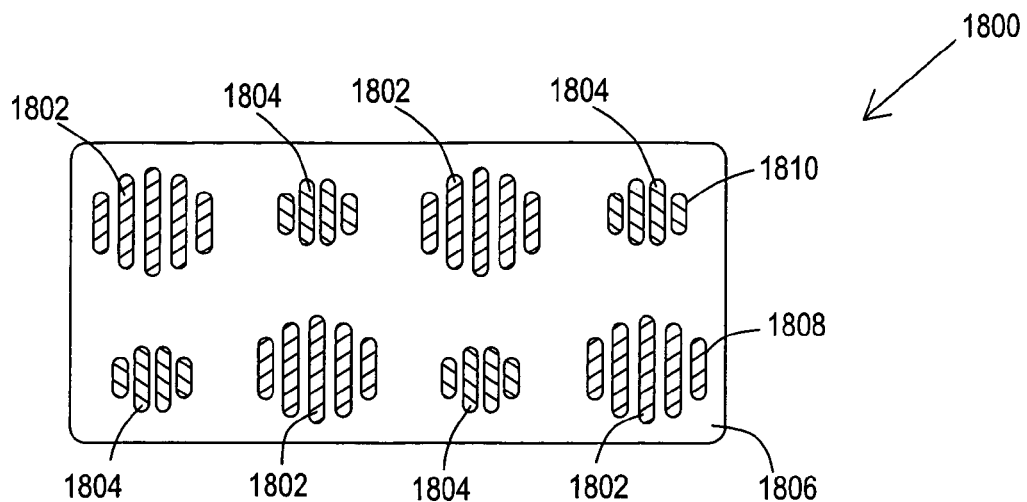
FIG. 18 is a cross-sectional, side view of a portion of a substrate having multiple first reservoirs and multiple second reservoirs embroidered to the substrate, in accordance with an example embodiment.

FIG. 18 is a top view of a portion of a footwear apparatus 1800 having one or more embroidered reservoirs, in accordance with an example embodiment. Apparatus 1800 includes multiple first reservoirs 1802 and multiple second, dissimilar reservoirs 1804. Selected ones of first reservoirs 1802 and/or second reservoirs 1804 may be formed from one or more "threads," which may be embroidered partially or completely through substrate 1806 and/or one or more layers of substrate 1806, if substrate 1806 is a multi-layer substrate. Although the term "thread" is used in describing various embodiments, it is to be understood that a "wire" may be substituted for a thread. In various embodiments, the term "embroidered" means sewn or stitched through.

Reservoirs 1802 and 1804 are illustrated as having threads 1808, 1810, respectively, embroidered in substantially parallel arrangement. It is to be understood that the threads of a reservoir may be embroidered in the alternate arrangements in order to produce a reservoir. Additionally, although reservoirs 1802, and 1804 are illustrated as having substantially circular perimeters or boundaries, it is to be understood that either or both types of reservoirs may have differently shaped perimeters or boundaries, including but not limited to shapes such as those illustrated in FIGS 1-13.

Figure 19:
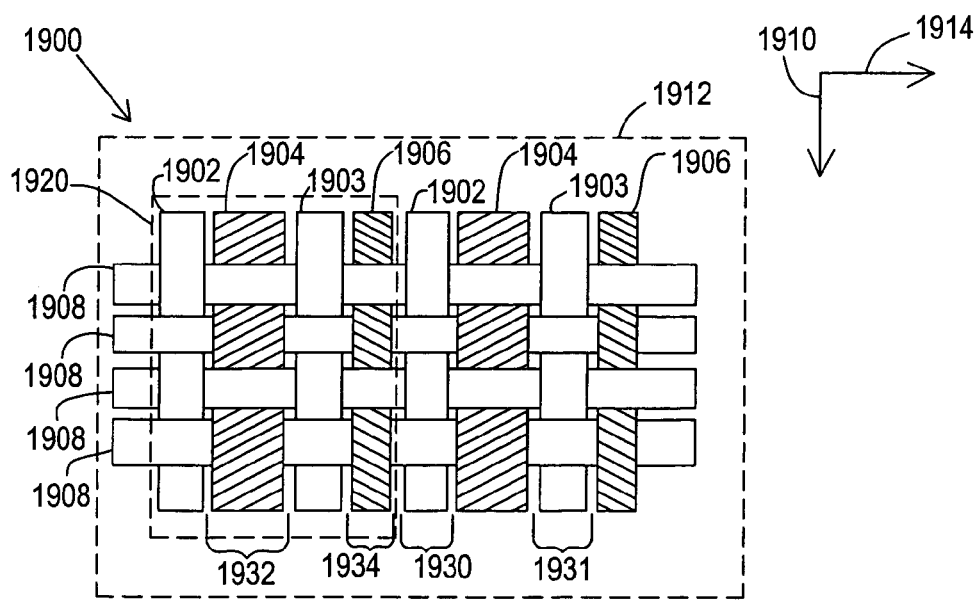
FIG. 19 is a top view of a portion of a footwear apparatus having a woven configuration of dissimilar reservoirs, in accordance with an example embodiment.

FIG. 19 is a top view of a portion of a footwear apparatus 1900 having a woven configuration of dissimilar reservoirs, in accordance with an example embodiment. The terms "weave" or "woven" are defined herein to mean any fabric structure that includes intertwined or interconnected threads, wires, yarns, or other elongate pieces, and further includes but is not limited to woven structures, knitted structures, braided structures, and the like.

Apparatus 1900 includes at least four elements, in an embodiment, which include parallel insulators 1902, 1903, first reservoirs 1904, second reservoirs 1906, and transverse insulators 1908. Each of parallel insulators 1902, 1903, first reservoirs 1904, second reservoirs 1906, and transverse insulators 1908 may be formed from one or more "threads" (e.g., first and second parallel insulator threads, first reservoir threads, second reservoir threads, and transverse insulator threads). Although the term "thread" is used in describing various embodiments, it is to be understood that a "thread" may include a "wire," and a wire may be substituted for a thread.

Parallel insulators 1902, 1903, first reservoirs 1904, and second reservoirs 1906 are arranged substantially parallel to each other, and oriented along a first direction 1910 across a plane 1912, in an embodiment. Additionally, in an embodiment, transverse insulators 1908 are woven in a second direction 1914 across plane 1912 through parallel insulators 1902, 1903, first reservoirs 1904, and second reservoirs 1906 in order to produce a woven apparatus 1900.

In an embodiment, parallel insulators 1902, 1903, first reservoirs 1904, and second reservoirs 1906 are sequentially arranged in a pattern which repeats when traveling in direction 1914. In an embodiment, a pattern repeat 1920 includes four pattern elements arranged next to and substantially parallel with each other: a) a first parallel insulator 1902, b) a first reservoir 1904, c) a second parallel insulator 1903, and d) a second reservoir 1906. In the illustrated embodiment, two pattern repeats 1920 are shown. In other embodiments, more or fewer pattern repeats may be included in an apparatus.

In an embodiment, a method of manufacturing woven apparatus 1900 may include weaving multiple first reservoirs 1904 together with multiple second reservoirs 1906, multiple parallel insulators 1902, and multiple transverse insulators 1908 to produce the pattern repeat discussed above. Selected ones of the multiple first reservoirs 1904 include a reducing agent, and selected ones of the multiple second reservoirs 1906 include an oxidizing agent.

Each insulator 1902, 1903, 1908, first reservoir 1904, and/or second reservoir 1906 may be formed from one or more substantially parallel, entwined, or braided threads. A thread diameter and/or number of threads within each parallel insulator 1902, 1903 may be selected to achieve desired separation distances 1930, 1931 between the perimeters of first reservoirs 1904 and the perimeters of second reservoirs 1906. In addition, a thread diameter and/or number of threads within a first reservoir 1904 and/or second reservoir 1906 may be selected to achieve a desired reservoir width 1932, 1934.

In an embodiment, first reservoir width 1932 may be in a range of approximately 0.5 millimeters (mm) to 4 mm (approximately 2 mm in a particular embodiment), and second reservoir width 1934 may be in a range of approximately 0.5 mm to 4 mm (approximately 1 mm in a particular embodiment). In other embodiments, either or both first reservoir width 1932 and/or second reservoir width 1934 may be slightly or significantly greater or smaller than the above-given range values.

In an embodiment, separation distances 1930, 1931 between first reservoirs 1904 and second reservoirs 1906 may be in a range of approximately 0.5 millimeters (mm) to 2.0 mm. In other embodiments, separation distances 1930, 1931 may be larger or smaller than the above-given range. Separation distances 1930, 1931 may be, in various embodiments, significantly smaller than the above-given range values. For example, an apparatus may include "nano-reservoirs," which may have widths measurable on a nanometer (nm) scale (e.g., from approximately 1 nm to approximately 10,000 nm or more). In such embodiments, separation distances 1930, 1931 may be in a range from approximately 1 nm to approximately 10,000 nm or more. In an embodiment, the physical separation between adjacent dissimilar reservoirs provides for substantial electrical isolation between the adjacent dissimilar reservoirs, absent an electrically conductive material provided between them.

First reservoirs 1904 include a first reservoir material and second reservoirs 1906 include a second reservoir material, in an embodiment. The first reservoir material of first reservoirs 1904 may include one or more first galvanic materials, and the second reservoir material of second reservoirs 1906 may include one or more second galvanic materials, in an embodiment. Various combinations of first and second galvanic materials are described later.

The first and/or second galvanic materials may be integrated within the threads of reservoirs 1904, 1906 and/or may be coated on the surfaces of the threads of reservoirs 1904, 1906, in various embodiments. In addition, in various embodiments, first and second reservoirs 1904, 1906 may include one or more structural materials, which may include, for example, but not by way of limitation, one or more materials selected from a group of materials that includes cotton, acetate, polyester, rayon, nylon, carbons, acrylic, plastics, polyethylene, polypropylene, silks, keratins (e.g., wool and/or camel hair), linen, various fiber blends, cellulosic fibers (e.g., wood pulp fibers, cotton fibers, hemp fibers, jute fibers, and/or flax fibers), ceramic fiber, acetates, cellulose esters, modacrylics, polymers, super-absorbent polymers (e.g., polymers capable of absorbing approximately 10 times their weight or greater), polyamides, polyolefins, polyvinyl alcohols, rubber, latex, and/or other materials. Insulators 1902, 1903, 1908 also may be formed from one or more of the above materials.

In another embodiment, first reservoirs 1904 and/or second reservoirs 1906 may include metal threads, such as purl or bullion threads, metallic passing threads, and/or metallized polyester, for example, but not by way of limitation. A metal thread may include, for example, a wire plated with silver, zinc, gold, tin, copper, nickel, alloys thereof, and/or other metallic plating materials. The wire may be formed of copper, steel, and/or other materials.

In an embodiment, insulators 1902, 1903, 1908 are substantially non-electrically conductive when not exposed to an activation material. In an embodiment, an activation material includes a conductive material. A conductive material may include, for example, a liquid (e.g., a solution, suspension, or emulsion), a semi-solid (e.g., a gel, cream, lotion, microemulsion or hydrogel), a solid, or a gaseous material.

The embodiment illustrated in FIG. 19 is illustrative of a woven embodiment. It is to be understood that various modifications of the pattern repeat, separation distances, sequence of pattern elements, direction of pattern elements, and other modifications could be made without departing from the scope of the inventive subject matter. In addition, in an embodiment, the first galvanic material may be integrated within the threads of an example embodiment, and a surface reservoir (e.g., reservoirs 102, FIG. 1) that includes the second galvanic material may be positioned in spaced relation to the first galvanic material containing threads, and vice versa.

Embodiments described herein may find application in a number of types of footwear apparatus. For example, but not by way of limitation, embodiments may be applied to a shoe, a shoe component, a shoe insert, a sock, and a therapeutic foot apparatus. FIGS. 20-26 illustrate a number of footwear apparatus with which embodiments may be used. These illustrations are for the purpose of example only, as there are numerous other configurations of footwear apparatus to which embodiments may be applied.

Figure 20:
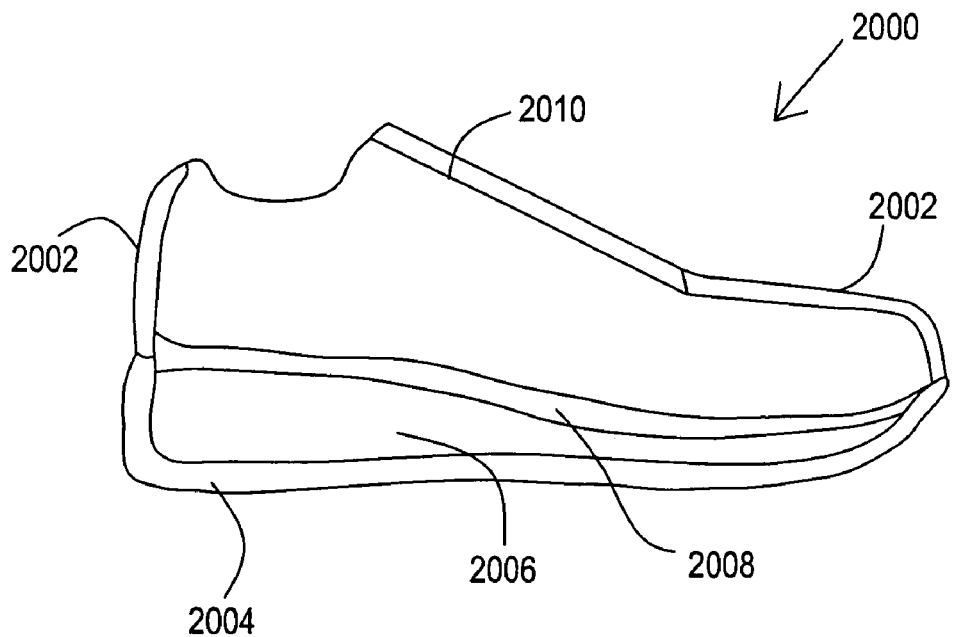
FIG. 20 is a cross-sectional, side view of a shoe, in accordance with an example embodiment.

FIG. 20 is a cross-sectional, side view of a shoe 2000, in accordance with an example embodiment. Although FIG. 20 illustrates an athletic shoe, it is to be understood that embodiments may also be applied to other types of shoes, including, but not limited to an athletic shoe, a sneaker, a dress shoe, a salon shoe, a loafer, a boot, a sandal, a water shoe, water fins (e.g., snorkeling fins), a specialty shoe (e.g., a military shoe/boot, medical personnel footwear, a construction shoe/boot, an operating room shoe, a golf shoe, a bowling shoe, a biking shoe, a track shoe, etc.), a waterproof shoe, a medical shoe for treatment of a malady (e.g., maladies discussed later), and/or a slipper.

Shoe 2000 includes several shoe components. In an embodiment, the shoe components include an upper 2002, outsole 2004, midsole 2006, and insole 2008. In addition, shoe 2000 may include a tongue 2010, a liner (not illustrated), and other components, such as a heel counter (not illustrated), stabilization elements (not illustrated), and so on. Some or all of shoe components 2002, 2004, 2006, 2008, 2010 may include one or more "foot-facing" surfaces and one or more other surfaces. As used herein, a "foot-facing" surface is a surface of a substrate, which directly or indirectly (e.g., through a sock or other layer) contacts or is oriented toward a foot, when the foot is inserted into the footwear apparatus.

Upper 2002 generally includes the top part of shoe 2000, which is adapted to hold a foot to the sole of the shoe. In an embodiment, upper 2002 includes a foot-facing surface 2020. Substantially all or portions of upper foot-facing surface 2020 may include embodiments of the inventive subject matter (e.g., discrete, dissimilar reservoirs) described in conjunction with FIGS. 1-19. Upper 2002 may be formed from one or more materials, including but not limited to leather, animal/plant-derived solid materials, nylon, polymers, textiles, and/or mesh materials, for example.

Outsole 2004 and midsole 2006 are secured to upper 2002. Insole 2008 may be secured to or placed within the cavity defined by midsole 2006 and upper 2002. Outsole 2004 includes the outer-most portion of shoe 2000, which is adapted to come into contact with the ground. Outsole 2004 may include a traction pattern on its bottom surface, and may be shaped according to the intended purpose (e.g., the sport) and/or playing surface. Outsole 2004 may be formed from one or more materials, including but not limited to rubber (e.g., blown rubber or carbon rubber), for example.

Midsole 2006 may be positioned between outsole 2004 and insole 2008. Midsole 2006 may include padding adapted to provide comfort, cushioning, and/or shock absorption. Midsole 2006 may be formed from one or more materials, including but not limited to ethylene vinyl acetate (EVA) foam, and/or polyurethane foam, for example. Midsole 2006 also may include other components, such as, for example, air bladders, stabilizing devices, honey-comb cut foam, and/or gel materials, to name a few.

Insole 2008 includes a portion of shoe 2000 above midsole 2006, forming a bottom, inside portion of shoe 2000. Insole 2008 may be removable or attached to midsole 2006. In an embodiment, insole 2002 includes a foot-facing surface 2022. Substantially all or portions of insole foot-facing surface 2022 may include embodiments of the inventive subject matter (e.g., discrete, dissimilar reservoirs) described in conjunction with FIGS. 1-19. Insole 2022 may include one or more layers, and may be formed from various materials, as will be discussed below. Various embodiments of insoles and other shoe inserts will be described in more detail in conjunction with FIGS. 21-23.

As used herein, a "shoe insert" includes, but is not limited to, a shoe pad, an insole, an arch support, an arch cushion, a heel cushion, a heel cup, a heel pad, a heel protector, a forefoot pad, a plantar pad, a dorsal foot pad, an orthotic device, a liner, a metatarsal pad, an insert portion of a shoe tree, and/or a shoe storage insert, for example. Several embodiments of shoe inserts are described in conjunction with FIGS. 21-23. It is to be understood that the illustrated embodiments are for the purpose of example, and that numerous other configurations of shoe inserts exist. Accordingly, the illustrated and described embodiments are not intended to limit the scope of the inventive subject matter only to those embodiments. It would be apparent to those of skill in the art, based on the description herein, to include discrete reservoirs on various other types of shoe inserts and/or shoe inserts having other physical configurations, layers, and/or materials.

Figure 21:
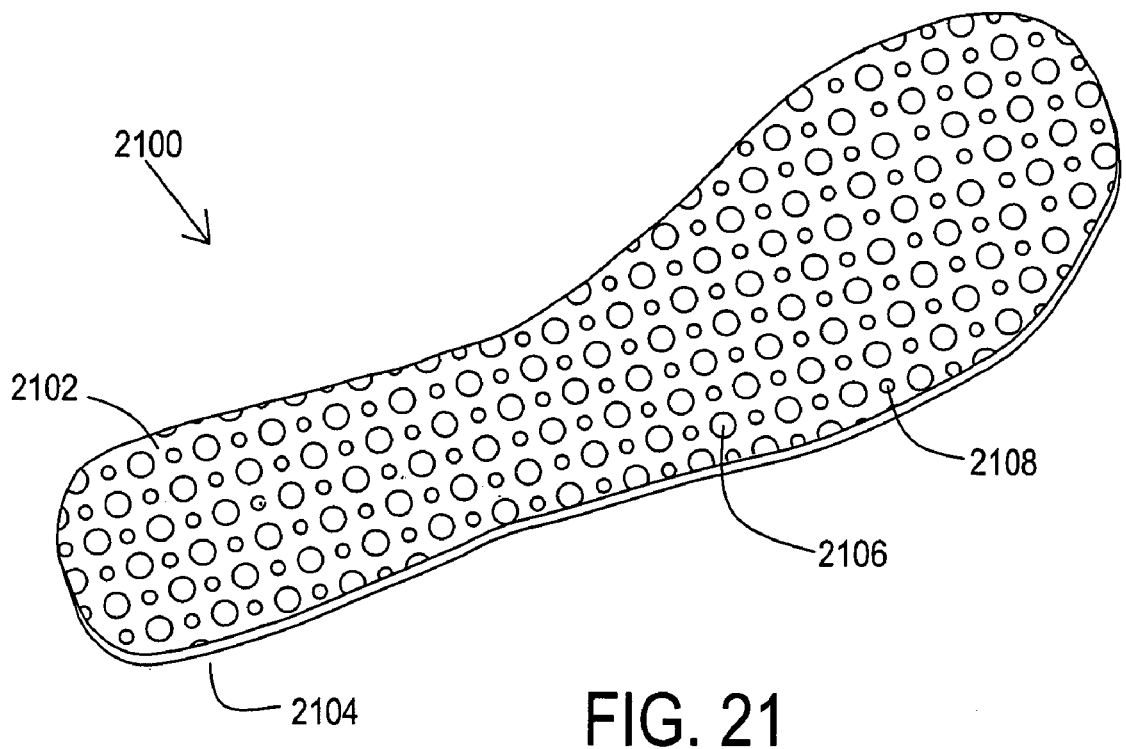
FIG. 21 is a perspective, exterior view of a shoe insert, in accordance with an example embodiment.

FIG. 21 is a perspective, exterior view of a shoe insert 2100, in accordance with an example embodiment. Shoe insert 2100 includes a foot-facing surface 2102 and a bottom surface 2104, in an embodiment. FIG. 21 illustrates an apparatus shaped to fit inside of a right shoe. It is to be understood, that an apparatus also may be shaped to fit inside of a left shoe or an apparatus may be shaped so as not to be differentiable between left or right.

In an embodiment, substantially all or portions of insert foot-facing surface 2102 may include embodiments of the inventive subject matter (e.g., discrete, dissimilar reservoirs) described in conjunction with FIGS. 1-19. In the illustrated embodiment, substantially all of foot-facing surface 2102 includes a first pattern of first reservoirs 2106 interleaved with a second pattern of second reservoirs 2108. In alternate embodiments, the distributions of reservoirs and/or the patterns may vary across foot-facing surface 2102, including having one or more regions without reservoirs. Also, in an embodiment, substantially all or portions of bottom surface 2104 may include embodiments of the inventive subject matter (e.g., discrete, dissimilar reservoirs).

Figure 22:
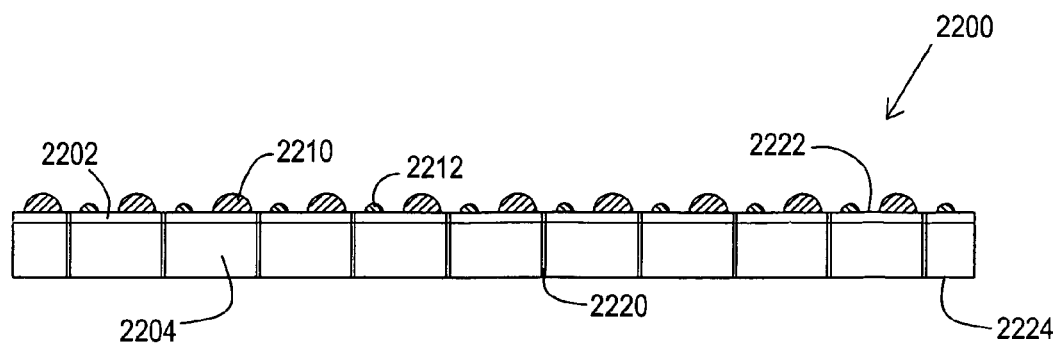
FIG. 22 is a cross-sectional, side view of a shoe insert, in accordance with an example embodiment.

FIG. 22 is a cross-sectional, side view of a shoe insert 2200, in accordance with an example embodiment. Shoe insert 2200 is substantially flexible, in various embodiments. Shoe insert 2200 includes a foot-contacting or top layer 2202 and at least one core layer 2204, in an embodiment. Although one top layer 2202 and core layer 2204 are illustrated, it is to be understood that more than two layers may be used.

Top layer 2202 may include a woven or non-woven material, in various embodiments. For example, in an embodiment, top layer 2202 may include a weave of cotton and acetate. In other embodiments, other woven and/or non-woven materials may be used for top layer 2202, including but not limited to one or more materials selected from a group of materials that includes cotton, acetate, polyester, rayon, nylon, carbons, acrylic, plastics, polyethylene, polypropylene, leather, animal/plant-derived solid materials, silks, keratins (e.g., wool and/or camel hair), linen, various fiber blends, cellulosic fibers (e.g., wood pulp fibers, cotton fibers, hemp fibers, jute fibers, and/or flax fibers), ceramic fiber, silk, acetates, cellulose esters, modacrylics, polymers, super-absorbent polymers (e.g., polymers capable of absorbing approximately 10 times their weight or greater), polyamides, polyolefins, polyvinyl alcohols, rubber, latex, and/or other materials. In an embodiment, top layer 2202 has a thickness in a range of about 0.2 to 0.4 mm. In other embodiments, top layer 2202 may be thicker or thinner than the above given range.

In an embodiment, shoe insert 2200 includes multiple first reservoirs 2210 and multiple second reservoirs 2212 joined with top layer 2202, wherein surfaces of reservoirs 2210, 2212 are proximate to the foot-facing or top surface 2212 of shoe insert 2200. As described previously, selected ones of the multiple first reservoirs 2210 may include a reducing agent, and selected ones of the multiple second reservoirs 2212 may include an oxidizing agent. Although a particular configuration of first and second reservoirs 2210, 2212 is illustrated in FIG. 22, other configurations of reservoirs may be used, including but not limited to those illustrated and described in conjunction with FIGS. 1-19.

In still other embodiments, top layer 2202 may include embroidered reservoirs, as discussed in conjunction with FIG. 18. The embroidered reservoirs may include reservoir threads that extend through top layer 2202 only, or may include reservoir threads that extend through top layer 2202 and core layer 2204, in various embodiments. In another embodiment, top layer 2202 may include a woven configuration of dissimilar reservoirs, as discussed in conjunction with FIG. 19.

In an embodiment, top layer 2202 and core layer 2204 are laminated together and are shaped (e.g., cut, stamped, or otherwise shaped) approximately to contour to the inside sole of an article of footwear, such as a shoe or boot. In other embodiments, layers 2202, 2204 may be stitched, stitch-bonded, connected using an adhesive, or otherwise connected together. In still another embodiment, layer 2202 may be formed in situ on layer 2204, or vice versa. Layers 2202 and 2204 may be considered a "substrate," in some embodiments.

Core layer 2204 may be formed of one or more flexible materials, including but not limited to one or more materials selected from a group of materials that includes rubber latex, latex foam, foam rubber, EVA, polyurethane, polypropylene, polyethylene foam, polyvinyl chloride, styrene-butadiene latex, polyolefin, polyester, visco-elastic polymer, cork, neoprene rubber, graphite, silicone, hydrogel, cellulosic fibers, or any other flexible material having adequate compressive strength. Core layer 2204 may have a thickness in a range of about 1.0 to 5.0 mm. In other embodiments, the thickness of layer 2204 may be greater or less than the above given range.

In an embodiment, shoe insert 2200 may include apertures 2220, which may include relatively small holes that extend vertically from the top surface 2222 of shoe insert 2200 toward the bottom surface 2224 of shoe insert 2200. In an embodiment, apertures 2220 are about 1 mm in diameter, and are spaced about 6 mm apart. In other embodiments, the diameter of apertures 2220 and/or the spacing between apertures 2220 may be greater or smaller than the above given values. In an embodiment, apertures 2220 pass through all layers 2222, 2224, and the entire shoe insert 2200 includes apertures 2220. In other embodiments, apertures 2220 may pass through fewer than all layers 2202, 2204, and/or less than the entire apparatus 2200 may include apertures 2220.

Although shoe insert 2200 is illustrated to include two layers 2202, 2204, additional layers may be included in other embodiments. For example, but not by way of limitation, shoe insert 2200 may include, for example, one or more additional layers formed from foam, woven or non-woven materials, paper, moisture-absorbing materials, or other materials. Additionally, some or all of the layers of shoe insert 2200 may be impregnated with, coated with, and/or have integrally included within them additional materials, such as fragrances, odor absorbing materials, activated charcoal, silica gel, and/or other materials.

Figure 23:
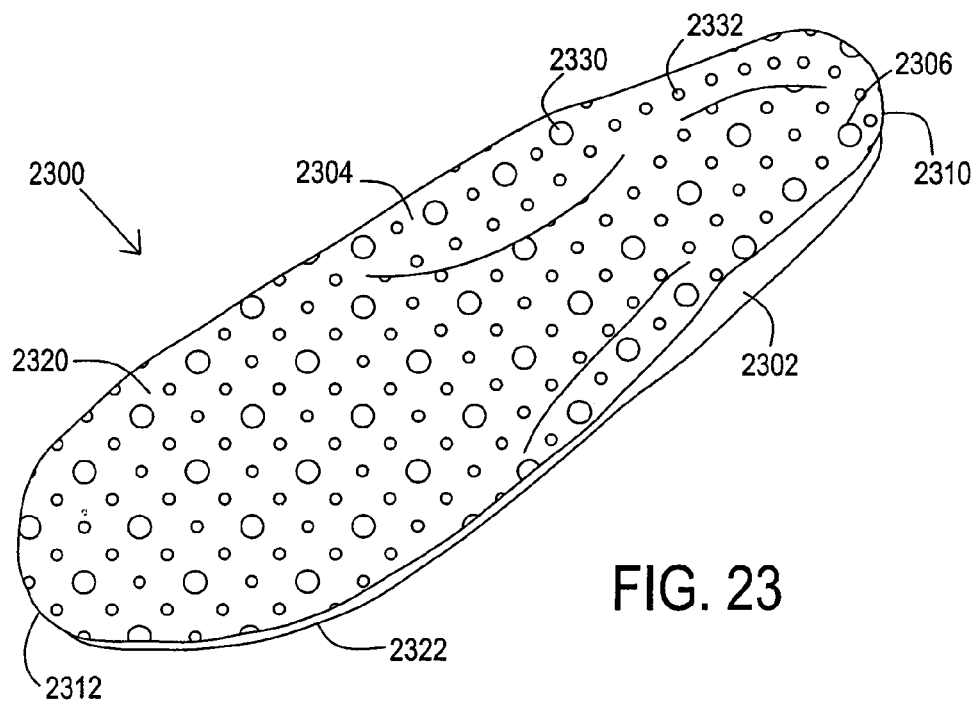
FIG. 23 is a perspective, exterior view of a shoe insert, in accordance with another example embodiment.

FIG. 23 is a perspective, exterior view of a shoe insert 2300, in accordance with another example embodiment. Shoe insert 2300 may include substantially rigid, semi-rigid, plastic, elastic, liquid, and/or substantially flexible portions, or may include a combination of various types of portions, in various embodiments.

Shoe insert 2300 includes a slab 2302. Slab 2302 may have various contours, as illustrated in FIG. 23, to provide support for various parts of the foot. Accordingly, slab 2302 may have thicknesses that vary in a range of about 1.0 to 15.0 mm. In other embodiments, the thicknesses of slab 2302 may be greater or less than the above given range.

In an embodiment, slab 2302 is shaped to fit within an article of footwear. Shoe insert 2300 includes an arch support 2304 and a heel cup 2306. Accordingly, slab 2302 may extend from a heel end 2310, corresponding to the rear of the heel of the foot, to a front end 2312, corresponding to the toes of the foot.

In other embodiments, a shoe insert may include other structural portions, and may be one or more apparatus selected from a group of apparatus that includes, but is not limited to, an insole, an arch support, an arch cushion, a heel cushion, a heel cup, a heel pad, a heel protector, a forefoot pad, a plantar pad, a dorsal foot pad, an orthotic device, and/or a metatarsal pad. Accordingly, slab 2302 may be longer or shorter than that illustrated in FIG. 23, and may be adapted to contact and/or provide support for different portions of the foot than the combination of the heel and the arch.

In various embodiments, slab 2302 may be cast or molded from one or more relatively rigid materials, may including but not limited to one or more materials selected from a group of materials that includes polyurethane, polypropylene, nylon, thermoplastic rubber, thermoplastic elastomer, other plastics, and/or other suitable elastomers. In various other embodiments, slab 2302 may be formed from or molded from one or more relatively flexible materials, including but not limited to one or more materials selected from a group of materials that includes rubber latex, latex foam, foam rubber, EVA, polyurethane, polypropylene, polyethylene foam, polyvinyl chloride, styrene-butadiene latex, polyolefin, polyester, visco-elastic polymer, cork, neoprene rubber, graphite, silicone, hydrogel, cellulosic fibers, or any other flexible material having adequate compressive strength.

Shoe insert 2300 includes a foot-facing or top surface 2320 and a bottom surface 2322, in an embodiment. In an embodiment, shoe insert 2300 includes multiple first reservoirs 2330 and multiple second reservoirs 2332 in proximity to and/or joined with foot-facing surface 2320. As described previously, selected ones of the multiple first reservoirs 2330 may include a reducing agent, and selected ones of the multiple second reservoirs 2332 may include an oxidizing agent. Although a particular configuration of first and second reservoirs 2330, 2332 is illustrated in FIG. 23, other configurations of reservoirs may be used, including but not limited to those illustrated and described in conjunction with FIGS. 1-19.

Although shoe insert 2300 is illustrated to be a single-component apparatus, additional components and/or layers may be included in other embodiments. For example, in various alternate embodiments, shoe insert 2300 may have a slab formed substantially of a first material, and one or more additional pads formed from another material, in various locations that correspond to high-impact points of the foot. In various other alternate embodiments, shoe insert 2300 may include a substantially flexible top layer (not illustrated), which may include a woven or non-woven material. Such a top layer may be similar to an embodiment of a top layer 2202, described in conjunction with FIG. 22.

Figure 24:
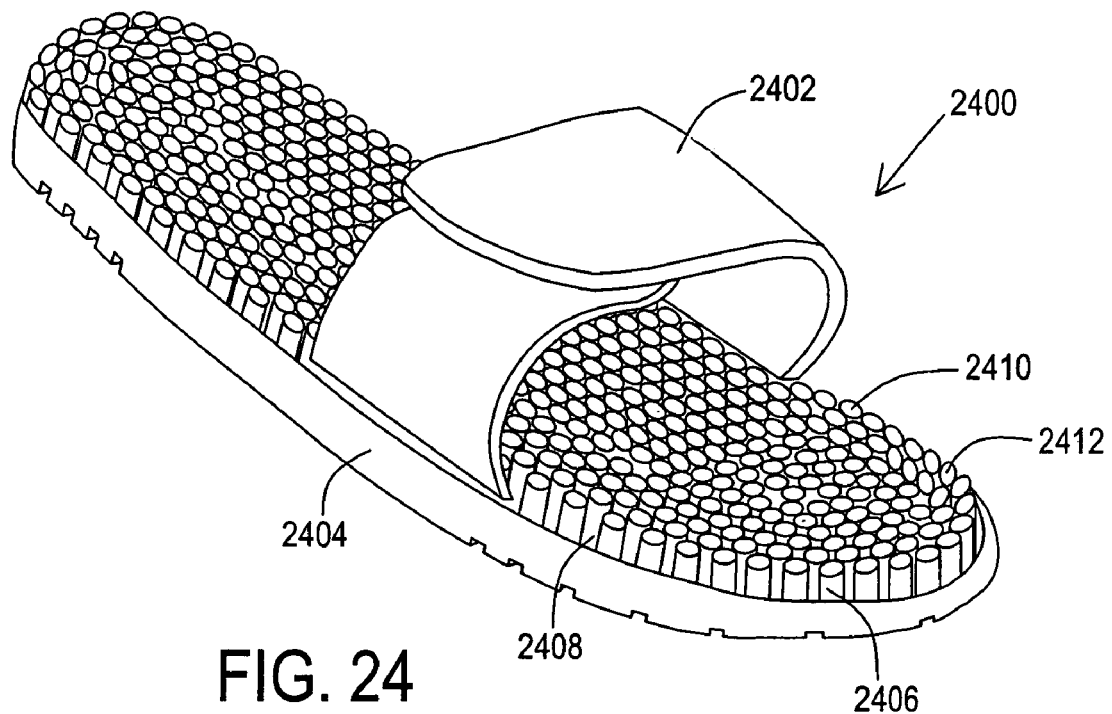
FIG. 24 is a perspective, exterior view of a sandal, in accordance with an example embodiment.

FIG. 24 is a perspective, exterior view of a sandal 2400, in accordance with an example embodiment. Sandal 2400 includes an upper 2402 and a sole 2404. Upper 2402 may be formed from any of a number of materials, including various plastics, woven or non-woven materials, leather, and/or animal/plant-derived solid materials, to name a few.

Sole 2404 may be considered a "foot-facing substrate," and may include multiple protrusions 2406, posts or bumps, in an embodiment, extending upwardly from foot-facing surface 2408. In an embodiment, multiple first reservoirs 2410 and multiple second reservoirs 2412 may be located in alternating positions in proximity to and/or joined with the tops of selected ones (e.g., some or substantially all) of protrusions 2406. In another embodiment, significant portions of protrusions 2406 may include reservoir material, such that, as the protrusions 2406 wear down through normal wear, additional reservoir material is exposed.

As described previously, selected ones of the multiple first reservoirs 2410 may include a reducing agent, and selected ones of the multiple second reservoirs 2412 may include an oxidizing agent. Although a particular configuration of first and second reservoirs 2410, 2412 is illustrated in FIG. 24, other configurations of reservoirs may be used. In other embodiments, sole 2404 may not include protrusions 2406. In alternate embodiments, patterns of first and second reservoirs 2410, 2412 may be located in proximity to or on foot-facing surface 2408 or on bumps on foot-facing surface 2408, rather than on protrusions 2406.

Sole 2404 may be cast or molded from a relatively rigid, semi-rigid, or relatively flexible material, including but not limited to one or more materials selected from a group of materials that includes polyurethane, polypropylene, nylon, thermoplastic rubber, thermoplastic elastomer, other plastics, other elastomers, rubber latex, latex foam, foam rubber, EVA, polyethylene foam, polyvinyl chloride, styrene-butadiene latex, polyolefin, polyester, visco-elastic polymer, cork, neoprene rubber, graphite, and/or silicone, for example.

Embodiments described in conjunction with FIGS. 20-24 may include reservoirs proximate to and/or present on various foot-facing or other surfaces or substrates. In still other embodiments, reservoirs also or alternatively may be proximate to and/or present on surfaces that are not foot-facing, and/or that are exterior to a shoe, shoe component, shoe insert, or sandal, or that are interior to portions of a shoe, shoe component, shoe insert, or sandal. For example, but not by way of limitation, reservoirs may be proximate to and/or present on any surface of a shoe, shoe component, shoe insert, and/or sandal, and/or may be located on one or more interior layers of a laminated or otherwise multi-layered footwear apparatus. Such reservoirs may function to reduce, eliminate or prevent the presence of potentially infectious agents (e.g., bacteria, mycobacteria, yeast, mold, virus, and/or fungus) within a footwear apparatus.

Figure 25:
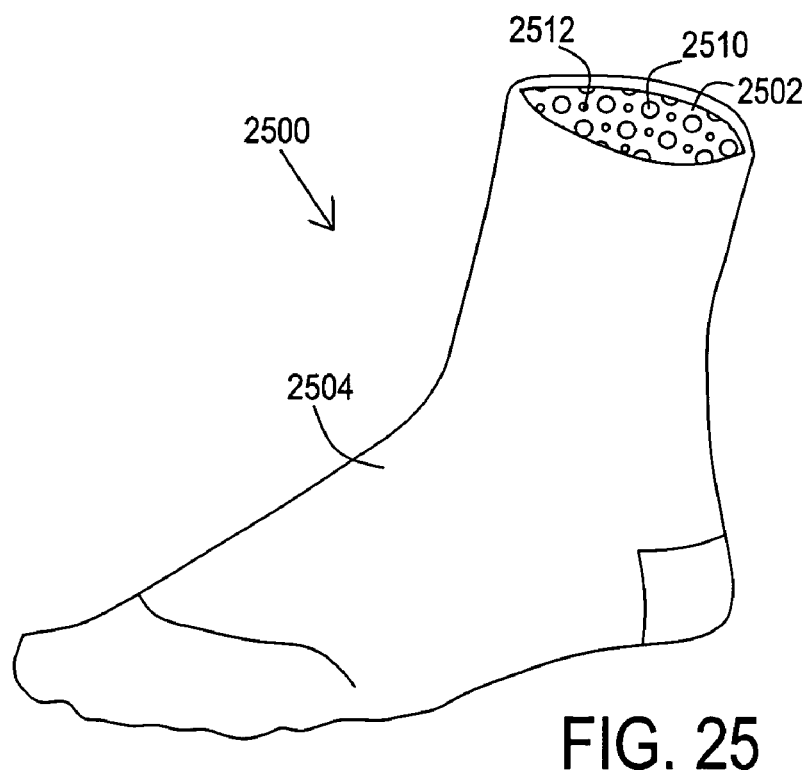
FIG. 25 is a perspective, exterior view of a sock, in accordance with an example embodiment.

FIG. 25 is a perspective, exterior view of a sock 2500, in accordance with another example embodiment. Although a traditional type of ankle sock is illustrated in FIG. 25, embodiments also include, but are not limited to, an calf-high sock, a knee-sock, a stocking, an ankle sleeve, a foot sleeve, a bunion brace and/or sleeve, an arch brace and/or sleeve, a toe(s) cot, a toe(s) sleeve, a venous anti-embolic stocking, and/or a pressure gradient stocking, for example.

Sock 2500 has an interior, foot-facing surface 2502 and an exterior surface 2504. In an embodiment, sock 2500 includes multiple first reservoirs 2510 and multiple second reservoirs 2512, wherein surfaces of reservoirs 2510, 2512 are proximate to foot-facing surface 2502 of sock 2500. In other embodiments, reservoirs 2510, 2512 may additionally or alternatively be proximate to exterior surface 2504. As described previously, selected ones of the multiple first reservoirs 2510 may include a reducing agent, and selected ones of the multiple second reservoirs 2512 may include an oxidizing agent. Reservoirs 2510, 2512 may be located across the entire foot-facing surface 2502 (e.g., the entire interior surface of sock 2500) or, in alternate embodiments, may be located only on portions of foot-facing surface 2502. For example, reservoirs 2510, 2512 may be located only in the foot region of the foot-facing surface 2502. In still other embodiments, sock 2500 may include embroidered reservoirs, as discussed in conjunction with FIG. 18, or sock 2500 may include a woven configuration of dissimilar reservoirs, as discussed in conjunction with FIG. 19.

Sock 2500 may include one or more materials, including but not limited to one or more materials selected from a group of materials that includes cotton, acetate, polyester, rayon, nylon, carbons, acrylic, plastics, polyethylene, polypropylene, leather, animal/plant-derived solid materials, silks, keratins (e.g., wool and/or camel hair), linen, spandex, neoprene rubber, elastic, rubber, ceramic fiber, various fiber blends, cellulosic fibers (e.g., wood pulp fibers, cotton fibers, hemp fibers, jute fibers, and/or flax fibers), ceramic fiber, silk, acetates, cellulose esters, modacrylics, polymers, super-absorbent polymers (e.g., polymers capable of absorbing approximately 10 times their weight or greater), polyamides, polyolefins, polyvinyl alcohols, latex, and/or other materials.

Although embodiments of a sock-type apparatus are described herein, it is to be understood that embodiments of the inventive subject matter also could be included within gloves and other types of sleeve-type apparatus, which are adapted to encompass other portions of the body (e.g., fingers, hands, arms, neck, torso, head, and legs).

Figure 26:
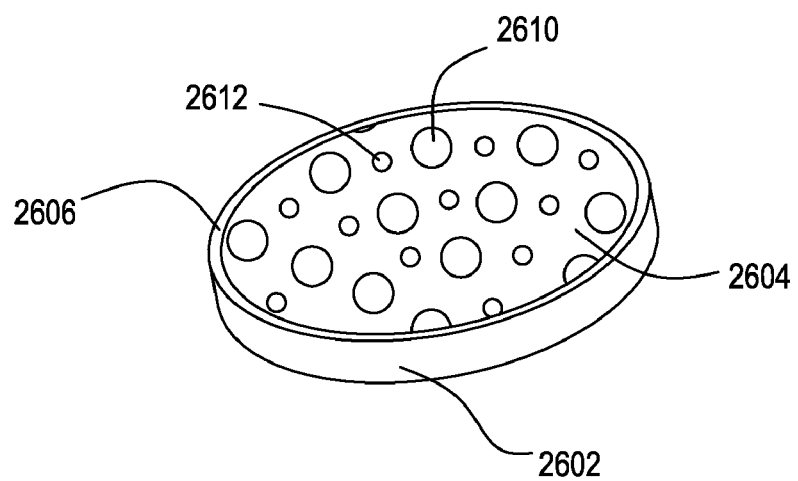
FIG. 26 is a perspective, exterior view of a therapeutic foot apparatus, in accordance with an example embodiment.

FIG. 26 is a perspective, exterior view of a therapeutic foot apparatus 2600, in accordance with another example embodiment. A therapeutic foot apparatus may include, for example, a callus cushion, a callus remover, a corn cushion, a corn remover, a wart remover, a blister pad, moleskin, an anti-microbial treatment barrier, a thin film (e.g., a self-adhesive thin film), and/or a cushioning pad, for example.

Therapeutic foot apparatus 2600 includes a substrate 2602 having a foot-facing surface 2604. In an embodiment, an adhesive material 2606 may be located across all or portions of foot-facing surface 2604. A protective liner (not illustrated) may be positioned over adhesive material 2606 prior to use.

In an embodiment, substrate 2602 may includes multiple first reservoirs 2610 and multiple second reservoirs 2612, wherein surfaces of reservoirs 2610, 2612 are proximate to foot-facing surface 2604 of substrate 2602. As described previously, selected ones of the multiple first reservoirs 2610 may include a reducing agent, and selected ones of the multiple second reservoirs 2612 may include an oxidizing agent. Reservoirs 2610, 2612 may be located across the entire foot-facing surface 2604 or, in alternate embodiments, may be located only on portions of foot-facing surface 2604. In still other embodiments, substrate 2602 may include embroidered reservoirs, as discussed in conjunction with FIG. 18, or substrate 2602 may include a woven configuration of dissimilar reservoirs, as discussed in conjunction with FIG. 19. In a particular embodiment, a thin film (e.g., a self-adhesive thin film) material may include first and second reservoirs, and the foot-facing surface of the film may be applied directly to an area of target tissue.

Substrate 2602 may include one or more of a number of materials selected from a group of materials that includes, but is not limited to, silicone, hydrogel, polymer gel, thermoplastic elastomer, wool, and felt, for example. Other materials may be used in other embodiments. In addition, substrate 2602 and/or adhesive material 2606 may include one or more therapeutic materials, such as salicylic acid, and/or antibiotics, for example.

Although the descriptions of various embodiments of footwear apparatus described herein may specify that reservoirs may be included on a particular footwear component and/or surface thereof, it would be apparent to one of skill in the art, based on the description herein, that reservoirs may be included on other footwear components and/or surfaces, in other embodiments. For example, but not by way of limitation, although embodiments are described above as including reservoirs on foot-facing surfaces, reservoirs may be alternatively or additionally included on non-foot-facing surfaces, such as exterior surfaces of the various footwear apparatus and/or surfaces of shoe storage inserts that are not adapted to contact a foot, but instead to contact the interior of a shoe.

In conjunction with FIG. 27, various embodiments for manufacturing a footwear apparatus will now be described, including but not limited to footwear apparatus embodiments previously described. In conjunction with these figures, some materials that may be used to form discrete reservoirs and substrates may be described in accordance with various embodiments. In addition, materials associated with conductive materials (e.g., activation materials) and other apparatus layers or elements may be described in accordance with various embodiments. It is to be understood that the inventive subject matter is not intended to be limited to the various materials described below. In alternative embodiments, various other materials may be used.

Figure 27:
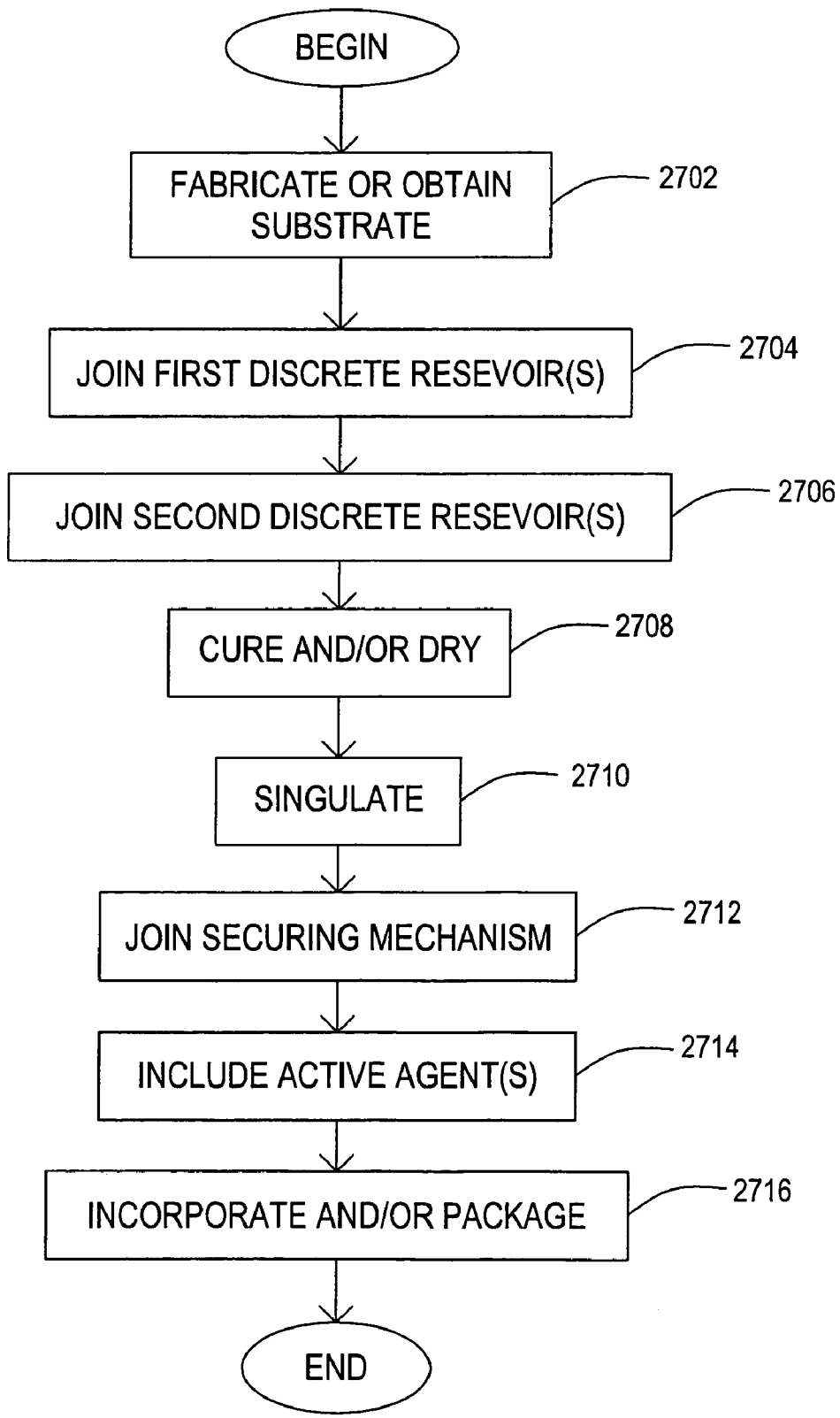
FIG. 27 is a flowchart of a method for manufacturing a portion of a footwear apparatus, in accordance with an example embodiment.

FIG. 27 is a flowchart of a method for manufacturing a footwear apparatus, in accordance with an example embodiment. It is to be understood that the processes described in conjunction with the flowchart may be performed in the illustrated order, or may be performed in alternative orders, while achieving substantially the same result. In addition, although the processes are illustrated as occurring consecutively. Some of the processes may be performed concurrently. Furthermore, some of the processes depicted in FIG. 27 may optionally be performed.

In an embodiment, a method for fabricating a footwear apparatus may begin by fabricating or obtaining a substrate having a first surface, in block 2702. A substrate may be formed from a bulk material and/or may include one or more similar or different material layers, sheets or films, in various embodiments.

A substrate may be fabricated into various shapes and sizes corresponding to a variety of target tissue types. A substrate may have a size and shape that may be useful in application to multiple anatomical areas or may have a size and shape that may be useful in application to specific target anatomical areas. In various embodiments, a substrate may be substantially two-dimensional (e.g., having relatively substantial dimensions in two orthogonal directions) or substantially three-dimensional (e.g., having relatively substantial dimensions in three orthogonal directions). As discussed previously, a substrate may be substantially rigid, semi-rigid, or substantially flexible. In various embodiments, a substrate may include one or more materials, such as the materials discussed previously.

In block 2704, the method continues by joining one or more first discrete reservoirs to the substrate. The method also includes joining one or more second discrete reservoirs to the substrate, in block 2706. In an embodiment in which the substrate is a multiple-layered substrate, blocks 2704 and 2706 may be performed on one or more layers prior to or after joining the multiple layers. For example, but not by way of limitation, the one or more first discrete reservoirs and the one or more second discrete reservoirs may be joined to a first layer of a multiple-layer substrate prior to joining the first layer to the other substrate layers. The processes associated with blocks 2704 and 2706 may be performed sequentially (in forward or reverse order) or simultaneously.

In an embodiment, the one or more first discrete reservoirs and the one or more second discrete reservoirs are joined to the substrate such that selected ones of the first and second reservoirs are physically separated, across a surface of the substrate, by substrate material. In an embodiment, the substrate material may be substantially electrically non-conductive. Accordingly, the physical separations between first and second reservoirs may provide for electrical isolation between the selected reservoirs, in the absence of a conductive material electrically interconnecting the reservoirs. In an alternate embodiment, the substrate material may include electrically conductive characteristics. In another alternate embodiment, one or more connecting elements may be joined to the substrate to interconnect selected ones of the first and second reservoirs.

In an embodiment, a pattern of multiple first discrete reservoirs and a pattern of multiple second discrete reservoirs are joined to the substrate in an interleaved configuration. In other embodiments, a single first discrete reservoir and/or a single second discrete reservoir are joined to the substrate.

The term "join" may be defined, in various embodiments, as including such processes as joining to a surface, adhering to a surface (e.g., using an adhesive), embedding into a hole or depression in a surface, layering onto a surface, and/or embroidering onto a substrate. In an embodiment that includes a weaved configuration (e.g., FIG. 19), "joining" may include the weaving process itself.

Embodiments of apparatus described herein include two or more types of dissimilar reservoirs, where a set of dissimilar reservoirs may form a galvanic cell. In another embodiment, an apparatus may include a first type of reservoir, and when the apparatus is brought into contact with an area of target tissue, the target tissue itself functions as a second, dissimilar reservoir. In such an embodiment, the apparatus' first reservoirs and the target tissue may form one or more galvanic cells.

Various materials may be selected for the first reservoir material and the second reservoir material. The first reservoir material and/or the second reservoir material may substantially include only a single galvanic material, or may include a composite or mixture of multiple galvanic and other materials.

In an embodiment, a first galvanic material included within a first reservoir provides for a first cell of a galvanic couple, and a second galvanic material included within a second reservoir provides a second cell of the galvanic couple. Examples of first galvanic material and second galvanic material combinations may include, but are not limited to, the following:

A) A first galvanic material including, but not limited to, zinc and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, and conductive carbon;

B) A first galvanic material including, but not limited to, magnesium and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, and conductive carbon;

C) A first galvanic material including, but not limited to, aluminum and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, and conductive carbon;

D) A first galvanic material including, but not limited to, iron, and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, and carbon;

E) A first galvanic material including, but not limited to, copper, and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, and conductive carbon; and F) A first galvanic material including, but not limited to, one or more of: zinc, magnesium, aluminum, iron, calcium, tin, copper, and alloys thereof; and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, carbon, and conductive carbon;

G) A first galvanic material including, but not limited to, one or more alloys of: zinc, magnesium, aluminum, iron, calcium, tin, copper, and alloys thereof; and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, carbon, and conductive carbon;

H) A first galvanic material including, but not limited to, one or more of: zinc, magnesium, aluminum, iron, calcium, tin, copper, and alloys thereof; and a second galvanic material including, but not limited to, one or more alloys of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, carbon, and conductive carbon;

I) A first galvanic material including, but not limited to, one or more alloys of: transitional metals including but not limited to zinc, manganese, scandium, titanium, vanadium, chromium, iron, cobalt, nickel, copper, cadmium, gold, mercury, platinum, iridium, osmium, tungsten, and rhenium; alkaline earth metals including but not limited to beryllium, magnesium, calcium, strontium, and barium; actinides including but not limited to aluminum, tin, gallium, indium, antimony, and bismuth; iodine, silicon, phosphorus, arsenic, selenium, cerium and alloys thereof, and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, carbon, and conductive carbon.

In the above lists of materials, the convention a/b may indicate a halide of "a." Accordingly, for example, the term "silver/silver chloride" indicates a silver halide Ag/AgCl. When halides are used in a first reservoir, an electrochemical reaction at the surface of a second reservoir may result in conversion of the halide to a pure metal (e.g., metallic silver) and halide ions. The terms "silver" and "metallic silver" may be used interchangeably herein. Use of the term "silver" includes "metallic silver."

The scope of the claimed subject matter is not meant to be limited to the above-listed galvanic material combinations. Further, a particular galvanic material may include multiple of the above-listed and/or other materials. In other embodiments, other materials may be selected for either or both a first galvanic material or a second galvanic material. For example, but not by way of limitation, one or more galvanic materials may include a polymer, fluid, gas or an organic material.

The first reservoir and/or the second reservoir may include the first galvanic material and the second galvanic material in the form of a solid bulk material, sheets, foils, crystals, flakes, wires, threads, slugs, pucks, disks, granules, needles, dust, powder, tubes, meshes, wools, rods, and/or shots, in various embodiments. For example, but not by way of limitation, in an embodiment, a first galvanic reservoir material may include silver crystals. In an embodiment, silver crystals may have sizes smaller than approximately 100 microns, although crystals having larger sizes may alternatively be used. In another embodiment, silver crystals may have average sizes of approximately 40 microns, although crystals having larger or smaller average sizes may alternatively be used. In an embodiment, a second galvanic reservoir material may include zinc crystals. In an embodiment, zinc crystals may have sizes smaller than approximately 100 microns, in an embodiment, although crystals having larger sizes may alternatively be used. In another embodiment, zinc crystals may have average sizes of approximately 40 microns, although crystals having larger or smaller average sizes may alternatively be used. In still other embodiments, silver and/or zinc crystals may have sizes in a range of approximately 1 to 10 microns.

The first reservoir and/or the second reservoir may include the first galvanic material and the second galvanic material in conjunction with a thread or wire, in various other embodiments. A thread may be coated with a coating that includes a first galvanic reservoir material or a second galvanic reservoir material. A wire may be coated with or include a first galvanic reservoir material or a second galvanic reservoir material. For example, but not by way of limitation, in an embodiment, a first galvanic reservoir material may include silver crystals. In an embodiment, silver crystals may have sizes smaller than approximately 100 microns, although crystals having larger sizes may alternatively be used. In another embodiment, silver crystals may have average sizes of approximately 40 microns, although crystals having larger or smaller average sizes may alternatively be used. In an embodiment, a second galvanic reservoir material may include zinc crystals. In an embodiment, zinc crystals may have sizes smaller than approximately 100 microns, in an embodiment, although crystals having larger sizes may alternatively be used. In another embodiment, zinc crystals may have average sizes of approximately 40 microns, although crystals having larger or smaller average sizes may alternatively be used.

According to various embodiments, the first and/or second reservoirs may be "reactive reservoirs" or "inert reservoirs." The term "inert reservoir" may be defined, in some embodiments, as a reservoir that may not undergo a significant change in its chemical composition during a redox reaction. In an embodiment, a reservoir may include or be coated with an inert material, so that an electrochemical process at the surface of the reservoir may generate oxidizing agents (e.g., nascent oxygen) and/or chlorine-containing oxidizing agents.

The term "reactive reservoir" may be defined, in some embodiments, as a reservoir that may undergo changes in its chemical composition during a redox reaction, which changes may occur when the apparatus is activated. In an embodiment, a reactive reservoir may include one or more reactive materials, which include but are not limited to, zinc, aluminum, copper, magnesium, manganese, silver, titanium, tin, iron, and alloys thereof. Upon passage of an electric current through a reactive reservoir, ions such as zinc, copper, magnesium, manganese, and/or aluminum cations may be released from the reservoir into a conductive material and/or into an area of target tissue. Such ions may or may not have therapeutic benefits, which may include, but are not limited to, anti-microbial effects, immunologic modulation, cellular and/or chemical transport properties, enzymatic regulation (including reaction catalysts), cellular induction, modulation of cellular differentiation and/or de-differentiation, modulation of cellular apoptosis, modulation of cellular morphology/genotype/phenotype, modulation of cellular function, modulation of cellular activity, modulation of cellular chemical activity and/or behavior, and/or anti-inflammatory effects.

In various embodiments, one or more additional materials may be included with the galvanic materials in the first reservoir material and/or the second reservoir material. In an embodiment, a galvanic material may be mixed with the one or more additional materials to form a reservoir material prior to joining the material with the substrate.

For example, but not by way of limitation, one or more soluble and/or insoluble binders may be included within a first reservoir material and/or a second reservoir material. A "binder" may be defined, in some embodiments, as a material that attaches other materials within a reservoir to a substrate. A binder may include, for example but not by way of limitation, a biocompatible liquid, a polymeric binder, a polyethylene binder, an acrylic binder, an ink (e.g., a polyacrylic ink), a paint, a pigment, an adhesive, and/or other materials. In other embodiments, a first reservoir material and/or a second reservoir material may not include a binder.

In an embodiment, a binder material may include a material that degrades (e.g., biodegrades, dissipates, breaks down, or is chemically or physically altered) in the presence of an activation material. As a binder material degrades, more galvanic material may be exposed to a reservoir surface. Eventually, substantially all material within a reservoir may degrade or change its structure or effect.

A type of binder selected and a ratio of binder material to galvanic material, within a reservoir, may be selected to affect a rate at which galvanic material and/or other materials are released from a reservoir (e.g., a rate at which a reservoir degrades). In an embodiment, a range of galvanic material percentages, by weight, within a reservoir material may be approximately 10% galvanic material to approximately 40% galvanic material. In another embodiment, a range of galvanic material percentages within a reservoir material may be approximately 1% galvanic material to approximately 10% galvanic material. In another embodiment, a range of galvanic material percentages within a reservoir material may be approximately 40% galvanic material to approximately 100% galvanic material. In other embodiments, different galvanic material percentage ranges may be included in a reservoir material.

The materials selected for the first and/or second reservoirs may be in a first state at the time they are joined to a substrate, and further processing steps may be performed to transform the materials to a second state. For example, various forming, curing, drying, and/or other processing procedures may be performed.

Referring again to FIG. 27, the apparatus may optionally be subjected to one or more curing and/or drying processes, in block 2708. Although a curing/drying process is illustrated to occur after joining one or more second discrete reservoirs to the substrate (block 2706), it is to be understood that a curing/drying process also may be performed prior to joining the one or more second reservoirs. In an embodiment, a curing/drying process may be performed after both blocks 2704 and 2706.

A curing or drying process may include exposing the apparatus to a heat source, frequency generator, chemical, wave generator, and/or light source for one or multiple time periods. Curing and/or drying may affect the characteristics of a first reservoir and/or a second reservoir. For example, a reservoir surface may be substantially smooth prior to curing or drying. Upon the performance of one or more curing or drying processes, surface discontinuities (e.g., cracks, holes, etc.) may be introduced. Such discontinuities may function to increase the effective surface area of a reservoir. Accordingly, rates of iontophoresis, reservoir material release, reservoir dissolution, and/or other processes may be affected.

Referring again to FIG. 27, in block 2710, a singulation process may optionally be performed to produce multiple footwear apparatus from the substrate. Singulation may include cutting, sawing, tearing, stamping or otherwise separating a substrate into multiple pieces. In another embodiment, one or more lines of perforation or indentation may be imprinted into a substrate surface or stamped through a substrate, to enable an end-user easily to singulate a footwear apparatus during future use.

In block 2712, a securing mechanism may optionally be joined to the apparatus. For example, in an embodiment, a securing mechanism may include an adhesive layer and/or a flexible sheet (e.g., formed from a material such as a polymer). In an embodiment, the adhesive layer may be covered by a removable liner sheet, to protect the adhesive from compromise prior to use.

As described previously, when a conductive material is brought in proximity to a galvanic cell, a redox reaction may occur between the cell components (e.g., a first reservoir and a second reservoir). In various embodiments, conductive materials included in a conductive material reservoir may include, but are not limited to, one or more of water, saline, organic or inorganic salts or buffers, electrolyte-active agents, hydrogel, and/or organic solvents. In other embodiments, redox reactions may occur when a galvanic cell is brought in proximity to another liquid material, a solid material, a semi-solid material, a gaseous material, wound exudation fluid and/or other biologically-produced fluids or conductive materials. Accordingly, these materials also may be considered to be activation materials. The term "biologic activation materials" may be defined, in some embodiments, as activation materials that are produced by a biologic entity.

An activation material may also include one or more additional materials, such as for example but not by way of limitation, one or more active agents, preservatives, stabilizing agents or antioxidants, pharmaceutical agents, hormones, growth factors, chelating agents, buffers, tonicity adjusting agents, suspending materials, and/or fluid-absorbing materials.

Referring back to FIG. 27, in block 2714, one or more active agents may optionally be incorporated into or onto an apparatus element, such as a substrate, one or more reservoirs, an activation material, or another apparatus component. In various embodiments, an active agent may be incorporated in the form of dissolved molecules and/or ions, dispersed solid particles, and/or liquid droplets (e.g., creams, lotions, emulsions, and/or liposome compositions). An "active agent" may include a synthetic compound or a compound isolated from a natural source, which has an effect on biologic tissue or cellular function, including but not limited to, a cosmetic effect, a therapeutic effect, a chemical effect, a morphologic effect, and/or a cellular effect, including but not limited to, cellular induction, modulation of cellular differentiation and/or de-differentiation, modulation of cellular apoptosis, modulation of cellular movement, modulation of cellular and/or chemical transport, modulation of cellular morphology, modulation of cellular function, modulation of cellular activity, modulation of cellular chemical activity and/or behavior. In various embodiments, an amount of active agent incorporated into or onto an apparatus element may be a "safe and effective amount" (e.g., from approximately 0.001% to about 20%, by weight, of the element into or onto which the active agent is incorporated).

Active agents may include, for example but not by way of limitation, one or more of a therapeutic drug (e.g., peptides, polypeptides, proteins, nucleic acid materials, hormones, growth factors, mitotic modulators, cytokines, interleukins, chelators, co-factors, trace minerals, fats, carbohydrates, complex molecules, and/or nutrients), wound-healing enhancing agents (e.g., recombinant human platelet-derived growth factor and/or other growth factors), salicylic acid, ketanserin, iloprost, scar-reducing agents, hair growth enhancing agents, hair growth retarding agents, antihypertensives, anticancer agents, endocrine and metabolic medication, neurologic medications, motion sickness reduction agents, protein and peptide drugs, anti-acne agent, anti-rosacea agent, anti-aging agent (e.g., sunscreens, vitamins, vitamin salts, alpha hydroxy acids and their precursors, beta hydroxyl acids, zinc and zinc-containing compounds, botanical extracts, and salts), pigmentation altering agents, plant extracts, metals, anesthetics, analgesics, drugs for treating psychiatric disorders, epilepsies, and migraine, drugs for stopping drug additions, anti-inflammatory agents, drugs to treat hypertension, cardiovascular diseases, gastric acidity and ulcers, drugs for hormone replacement therapies and contraceptives, antibiotics, antibacterial agents, antimold agents, antifungal agents, antiviral agents, antipsoriatic agents, antimicrobial agents, anti-inflammatory agents, antineoplastic agents, immunosuppressive agents, immunostimulants, drugs acting on blood and blood forming organs, vaccines, and/or antivenins.

Referring again to FIG. 27, in block 2716, the apparatus may optionally be incorporated as part of a footwear apparatus and/or packaged. In an embodiment, packaging includes providing a covering over the apparatus, which protects the apparatus from environmental or physical damage, prior to use. The method then ends.

The apparatus illustrated in FIG. 1-26 may be "activated" in one or more of several ways. In an embodiment, activation occurs when a conductive material is located between the reservoirs such that electrical communication and/or ionic communication may occur between the reservoirs through the conductive material. When a conductive material is between the dissimilar galvanic reservoirs, currents may be produced proximate to a surface of a substrate. In various embodiments, these currents may have therapeutic effects, as will be described later.

The conductive material may be proximate to the target tissue area, and/or the conductive material may be applied to the apparatus. For example, in an embodiment, sweat, water, saline, joint fluid, cyst fluid, wound exudation fluid, blood, and/or other biologic fluids or materials proximate to the area of target tissue may function as an activation material when it is proximate to the reservoirs. In other embodiments, an activation material may be provided with the apparatus. For example, an activation material may be included within an activation material reservoir, which may be selectively opened or broken to release an activation material onto the apparatus and/or onto a surface of the target tissue area. Alternatively, an activation material may be provided as a solid, semi-solid, liquid, or gaseous material that may otherwise be applied to the dressing and/or an area of target tissue.

Figure 28:
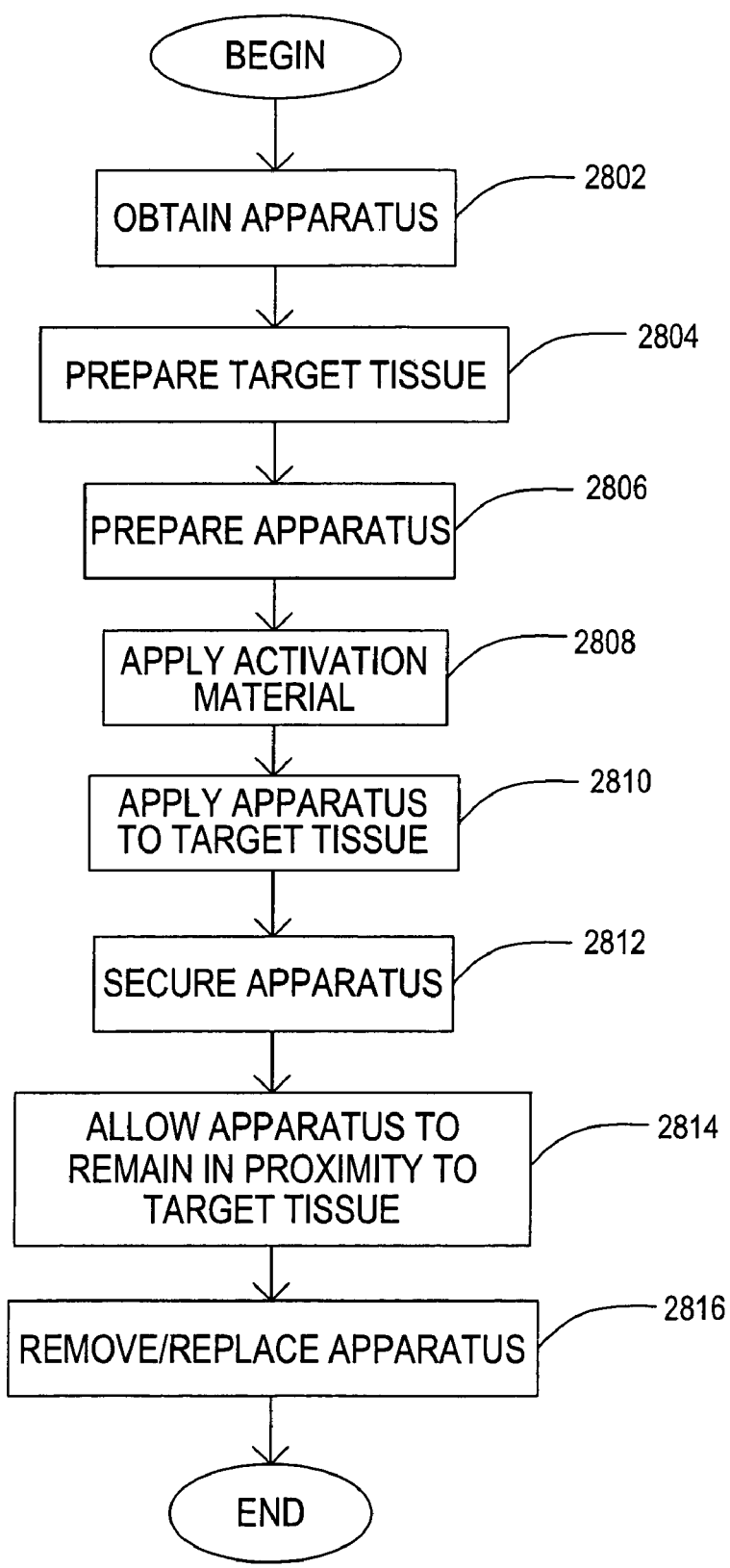
FIG. 28 is a flowchart of a method for using a footwear apparatus, in accordance with an example embodiment.

FIG. 28 is a flowchart of a method for using a footwear apparatus, in accordance with an example embodiment. In block 2802, an apparatus may be obtained, which includes an embodiment of the inventive subject matter.

In block 2804, an area of target tissue optionally may be prepared for application of the apparatus. Preparation of the target tissue may include one or more processes such as cleaning the area of target tissue, making one or more incisions to expose the area of target tissue, resurfacing the area of target tissue, and/or any of a number of other processes. In an alternate embodiment, no target tissue preparation may be performed.

In block 2806, the apparatus optionally may be prepared for application to a target tissue area. For example, but not by way of limitation, the apparatus may be removed from protective packaging, the apparatus may be cut or torn to size, and/or one or more release liners may be removed from the apparatus.

In block 2808, an activation material optionally may be applied to the apparatus and/or to the target tissue area. For example, but not by way of limitation, a conductive material may be released from an activation material reservoir associated with the apparatus, or another type of activation material associated with the apparatus may be placed in contact with the apparatus and/or the area of target tissue. In alternate embodiments, an activation material may not be applied, and the apparatus may be activated when it comes into contact with activation material proximate to the target tissue area.

In block 2810, the apparatus may be applied proximate to the target tissue area. In an embodiment, application of the apparatus may result in currents between dissimilar reservoirs contacting (e.g., penetrating or contacting the surface of) the target tissue area. Alternatively or in addition, application may result in currents electromotivating therapeutic materials toward the target tissue area. Application of the apparatus may result in additional or different effects, in other embodiments.

In block 2812, the apparatus optionally may be secured to tissue or structures proximate to the target tissue area. The apparatus may be secured using a securing mechanism associated with the apparatus, a securing mechanism distinct from the apparatus, and/or by tissue and/or other structures proximate to the target tissue area.

In block 2814, the apparatus optionally may be allowed to remain in proximity to the target tissue area for a period of time, referred to as a "period of application." A period of application of an apparatus may be shorter than, approximately equal to, or longer than an apparatus "period of effectiveness." A "period of effectiveness" may be defined, in some embodiments, as a period of time during which an apparatus may or may not perform a beneficial activity (e.g., production of currents, iontophoresis, supply of anti-bacterial or other therapeutic materials, etc.). A period of effectiveness may depend on one or more of several factors, including the materials, material concentrations, and material orientations within the apparatus, the conductive material, ambient conditions (e.g., temperature, target tissue characteristics, etc.), and other factors. In an embodiment, an apparatus may have a period of effectiveness in a range from approximately 1-14 days, although an apparatus may have a period of effectiveness that is longer or shorter than this range, in other embodiments. In an embodiment, the first reservoirs and the second reservoirs are configured to sustain the one or more currents for approximately a pre-determined period of time (e.g., a pre-determined period of effectiveness).

In block 2816, an apparatus optionally may be removed and/or replaced, in an embodiment. In an alternative embodiment, an apparatus may remain in proximity to an area of target tissue indefinitely. The method then ends.

Applications or uses for embodiments of the inventive subject matter may include any one or more of several types of methods of use. For example, but not by way of limitation, the terms "methods of application" or "methods of applying" may include, but are not limited to, one or more of the following:

1) methods of treatment to enhance healing of breached or compromised biologic tissue and/or tissue disorders;

2) methods to apply electricity to an area of biologic tissue to provide therapeutic results;

3) methods to alter the appearance of a tissue condition;

4) methods to provide or enhance the delivery of therapeutic materials to an area of biologic tissue and/or to a biologic system through an area of biologic tissue;

5) methods to reduce or eliminate infections (e.g., bacterial, mycobacterial, yeast, mold, viral, and/or fungal infections) within an area of biologic tissue and/or within a biologic system;

6) methods to reduce a likelihood for infections (e.g., bacterial, mycobacterial, yeast, mold, viral, and/or fungal infections) within an area of biologic tissue and/or within a biologic system;

7) methods to alter the cellular activity of an area of biologic tissue and/or within a biologic system (e.g., cellular induction, modulation of cellular differentiation and/or de-differentiation, modulation of cellular apoptosis, modulation of cellular morphology, modulation of cellular function, modulation of cellular activity, modulation of cellular movement/migration, modulation of cellular transport, modulation of cellular chemical activity and/or behavior);

8) methods to reduce pain and/or other irritation (e.g., itching) at an area of biologic tissue; and/or 9) methods to reduce, eliminate or prevent the presence of potentially infectious agents (e.g., bacteria, mycobacteria, yeast, mold, virus, and/or fungus) within a physical structure (e.g., a footwear or other apparatus).

In various embodiments, methods of achieving various affects on biologic tissue and/or biologic systems may include applying embodiments of apparatus to an area of biologic tissue proximate to a foot. An area of biologic tissue selected for application of an embodiment may include biologic tissue selected from a group that includes, but is not limited to, damaged biologic tissue, inflamed biologic tissue, diseased biologic tissue, infected biologic tissue, healthy biologic tissue, and combinations thereof.

The terms "treat," "treating," and "treatment" may be defined, in some embodiments, as the treatment (e.g., alleviation or elimination of symptoms and/or cure) and/or prevention or inhibition of a condition or disorder of tissue or a biologic system. The terms "condition" and "disorder," may be defined, in some embodiments, as diseases, disorders, and/or characteristics of tissue. The term "enhance healing of" may be defined, in some embodiments, as improve results of healing, reduce scarring during healing, accelerate healing, induce healing, and/or expedite healing.

In various embodiments, methods of application (e.g., embodiments of FIG. 28) may include methods to treat and/or to enhance healing of breached or compromised biologic tissue, where the tissue may include one or more conditions selected from a group that includes, but is not limited to, an infected traumatic lesion, a surgical incision, a lesion, a wound, a cut, a puncture, a rupture, an abrasion, a laceration, a biopsy site, post-laser treated skin, post-chemical peeled skin, a burn, sunburn, frostbite, an ulcer (e.g., diabetic, venous stasis, etc.), a bed sore, a rash, dermatitis, hypertrophic skin disorders, proliferative skin disorders, contact dermatitis (e.g., from poison ivy/poison oak exposure), an insect bite and/or sting, a snake bite, a human bite, and an animal bite.

In various embodiments, methods of application (e.g., embodiments of FIG. 28) may include methods to treat and/or enhance healing of conditions of the foot, toes, toenails, ankle, and lower leg, where the conditions may include one or more conditions selected from a group that includes, but is not limited to, actinic keratosis, kaposi's sarcoma, pigmented lesions, melanomas (e.g., malignant melanoma), venous stasis ulcers, diabetic ulcers, ischemia ulcers, diabetic dermopathy, diabetic neuropathy, eczema, hypertrophic skin disorders, proliferative skin disorders, dermatitis, bromhidrosis, foot odor, tenia pedis (athlete's foot), fungal infections, blisters, abrasions, skin tears, corns, warts (e.g., verruca vulgaris), calluses, gangrene, fissures (e.g., cracking of the skin), abscesses, cellulites, psoriasis, hyperhidrosis, erythromelalgia, peripheral nerve compression, neuroma, plantar fasciitis, ingrown toenails, tumors, and ganglion.

In various embodiments, methods of application (e.g., embodiments of FIG. 28) may include methods to treat and/or to enhance healing of skin, hair, and nail conditions, where the conditions may include one or more conditions selected from a group that includes, but is not limited to, a bacterial infection, a mycobacterial infection, a yeast infection, a fungal infection, a mold infection, a viral infection, a scar, acne, blisters, a corn, a callus, dermatographia, hives, angioedema, psoriasis, rosacea, scabies, vitiligo, dysplasia, dermatitis, eczema, ecthyma, atopic dermatitis, dyshidrosis, neurodermatitis, a boil, carbuncles, cellulitis, a cold sore, folliculitis, furunculosis, impetigo, jock itch, molluscum conagiosum, herpes, Mucha-Havermann disease, ringworm, shingles, chickenpox, tinea versicolor, actinic keratosis, a wart, freckles, a mole, unusual pigmentation, lipoma, melanoma, scalp cancer, skin cancer, acanthosis nigricans, bullous pemphigoid, epidermolysis bullosa, icthyosis, pityriasis rosea, granuloma annulare, hidradenitis, lichen nitidus, lichen planus, morphea, scleroderma, pilonidial cysts, pyoderma gangrene, Stevens-Johnson syndrome, hemangioma, sweating, body odor, cercarial dermatitis, and/or a nail fungal infection.

Application of an embodiment of the invention to an area of target tissue may or may not produce one or more beneficial results, including but not limited to:

a) stimulation of fibroplasia (e.g., regeneration of connective tissue);

b) stimulation of epithelialization (e.g., regeneration of skin);

c) collagen remodeling (e.g., reforming of collagen fibrils);

d) stimulation of neoangiogenesis (e.g., regenerating blood supply to tissue);

e) anti-microbial action (e.g., attraction of microbes toward a reservoir, and neutralization or elimination of the microbes through contact with reservoir material);

f) providing an electromotive force to drive one or more materials (e.g., silver and/or zinc) toward and/or into an area of target tissue (e.g., iontophoresis), which may or may not have an effect of killing microbes, and/or moving or attracting electrically charged healing cells;

g) electrically attracting microbes proximate to or within an area of target tissue to a reservoir, and when the reservoir includes anti-microbial materials, killing the attracted microbes;

h) stimulating, augmenting, or simulating biologic currents normally produced and present at acute tissue injury sites;

i) wound contraction;

j) providing wound healing stimulus across an entire wound surface by providing current over the wound surface (e.g., simulating a current of injury usually found around a periphery of a wound to an entire wound surface);

k) alteration of capillary permeability;

l) cellular migration and transport;

m) changing cellular activity from hypoactive or hyperactive to normal (e.g., in a state of homeostasis);

n) modifying cellular induction, modulation of cellular differentiation and/or de-differentiation, modulation of cellular apoptosis, modulation of cellular morphology, modulation of cellular function, modulation of cellular activity, modulation of cellular chemical activity and/or behavior, modulation or cellular transport, modulation of cellular migration; and/or o) pain reduction.

Thus, various embodiments of medical apparatus and methods of use and manufacture have been described. The foregoing description of specific embodiments reveals the general nature of the inventive subject matter sufficiently that others can, by applying current knowledge, readily modify and/or adapt it for various applications without departing from the general concept. Therefore, such adaptations and modifications are within the meaning and range of equivalents of the disclosed embodiments.

The phraseology or terminology employed herein is for the purpose of description and not of limitation. Accordingly, the inventive subject matter embraces all such alternatives, modifications, equivalents and variations as fall within the spirit and broad scope of the appended claims.

What is claimed is:

1. A method of manufacturing a footwear apparatus, the method comprising:
    joining, with a substrate, multiple first reservoirs wherein selected ones of the multiple first reservoirs include a reducing agent, and wherein first reservoir surfaces of selected ones of the multiple first reservoirs are proximate to a first substrate surface; and
    joining, with the substrate, multiple second reservoirs wherein selected ones of the multiple second reservoirs include an oxidizing agent, and wherein second reservoir surfaces of selected ones of the multiple second reservoirs are proximate to the first substrate surface, wherein joining the multiple first reservoirs and joining the multiple second reservoirs comprises:
        combining the multiple first reservoirs, the multiple second reservoirs, and multiple parallel insulators to produce a pattern repeat arranged in a first direction across a plane, the pattern repeat including a sequence of a first one of the parallel insulators, one of the multiple first reservoirs, a second one of the parallel insulators, and one of the multiple second reservoirs; and
        weaving multiple transverse insulators through the first parallel insulator, the one first reservoir, the second parallel insulator, and the one second reservoir in a second direction across the plane to produce a woven apparatus.

2. A fabric structure comprising:
    a substrate;
    multiple first reservoirs joined with the substrate, wherein selected ones of the multiple first reservoirs include a reducing agent, and wherein first reservoir surfaces of selected ones of the multiple first reservoirs are proximate a first substrate surface;
    multiple second reservoirs joined with the substrate, wherein selected ones of the multiple second reservoirs include an oxidizing agent, and wherein second reservoir surfaces of selected one of the multiple second reservoirs are proximate the first substrate surface;
    a first insulator formed from at least one first parallel insulator thread arranged in a first direction across a plane;
    the multiple first reservoirs include a first reservoir formed from at least one first reservoir thread, the first reservoir being arranged next to and substantially parallel to the first insulator;
    a second insulator formed from at least one second parallel insulator thread arranged next to and substantially parallel to the first reservoir; and
    the multiple second reservoirs include a second reservoir formed from at least one second reservoir thread, the second reservoir being arranged next to and substantially parallel to the second insulator.

3. The fabric structure of claim 2, further comprising:
    at least one transverse insulator, formed from at least one transverse insulator thread, woven through the first insulator, the first reservoir, the second insulator, and the second reservoir in a second direction across the plane.

* * * * *